(12) United States Patent
Adachi et al.

(10) Patent No.: US 11,775,069 B2
(45) Date of Patent: Oct. 3, 2023

(54) REMOTE CONTROL DEVICE FOR MEDICAL SYSTEM

(71) Applicant: J. MORITA MFG. CORP., Kyoto (JP)

(72) Inventors: Koichiro Adachi, Kyoto (JP); Seiichiro Yamashita, Kyoto (JP); Kyohei Kato, Kyoto (JP)

( * ) Notice: Subject to any disclaimer, the term of this patent is extended or adjusted under 35 U.S.C. 154(b) by 0 days.

(21) Appl. No.: 17/148,560

(22) Filed: Jan. 14, 2021

(65) Prior Publication Data

US 2021/0225140 A1    Jul. 22, 2021

(30) Foreign Application Priority Data

Jan. 17, 2020    (JP) ................................. 2020-005838
Jan. 17, 2020    (JP) ................................. 2020-005839

(51) Int. Cl.
*G06F 3/01* (2006.01)
*G06F 3/04817* (2022.01)
(Continued)

(52) U.S. Cl.
CPC ............ *G06F 3/016* (2013.01); *A61B 5/0002* (2013.01); *A61B 5/002* (2013.01); *A61B 5/7405* (2013.01);
(Continued)

(58) Field of Classification Search
CPC .. G06F 3/016; G06F 3/04817; G06F 3/04847; G06F 3/0485; G06F 3/04883;
(Continued)

(56) References Cited

U.S. PATENT DOCUMENTS

| 2002/0182564 A1 | 12/2002 | Katsuda et al. |
| 2005/0042572 A1 | 2/2005 | Katsuda et al. |

(Continued)

FOREIGN PATENT DOCUMENTS

| EP | 3309794 | 4/2018 |
| EP | 3391867 | 10/2018 |

(Continued)

OTHER PUBLICATIONS

Meghan Woo and Olivia Bacon, Making Healthcare Safer III: A Critical Analysis of Existing and Emerging Patient Safety Practices—§ 13 Alarm Fatigue, available at https://www.ncbi.nlm.nih.gov/books/NBK555526/pdf/Bookshelf_NBK555526.pdf (Mar. 2020) (Year: 2020).*

(Continued)

*Primary Examiner* — Justin R. Blaufeld
(74) *Attorney, Agent, or Firm* — SOEI PATENT & LAW FIRM

(57) ABSTRACT

In a medical system, a medical device includes a first display that displays a figure or a character corresponding to data relevant to medical treatment performed in the medical device, and a first controller that causes the first display to display the figure or the character corresponding to the data and that, when the data satisfies conditions for notification of a warning, causes the medical device to emit a first warning. A remote control device includes a second display that displays the figure or the character corresponding to the data, and a second controller that causes the second display to display the figure or the character corresponding to the data and that, when the data satisfies the conditions for notification of the warning, causes the remote control device to emit a second warning that is different than the first warning.

20 Claims, 15 Drawing Sheets

(51) Int. Cl.
G06F 3/04847 (2022.01)
G06F 3/0485 (2022.01)
G06F 3/04883 (2022.01)
G06F 3/16 (2006.01)
G16H 40/63 (2018.01)
A61B 5/00 (2006.01)
A61C 1/00 (2006.01)
A61C 19/04 (2006.01)

(52) U.S. Cl.
CPC ............ *A61B 5/746* (2013.01); *A61B 5/7435* (2013.01); *A61B 5/7445* (2013.01); *A61B 5/7455* (2013.01); *G06F 3/0485* (2013.01); *G06F 3/04817* (2013.01); *G06F 3/04847* (2013.01); *G06F 3/04883* (2013.01); *G06F 3/165* (2013.01); *G16H 40/63* (2018.01); *A61B 5/0022* (2013.01); *A61C 1/0015* (2013.01); *A61C 19/041* (2013.01)

(58) Field of Classification Search
CPC ....... G06F 3/165; G16H 40/63; A61B 5/0002; A61B 5/002; A61B 5/7405; A61B 5/7435; A61B 5/7445; A61B 5/7455; A61B 5/746; A61B 5/0022; A61C 1/0015; A61C 19/041
See application file for complete search history.

(56) References Cited

U.S. PATENT DOCUMENTS

| | | | |
|---|---|---|---|
| 2005/0151640 A1* | 7/2005 | Hastings | G16H 40/67 340/539.11 |
| 2006/0220881 A1* | 10/2006 | Al-Ali | A61B 5/0022 600/310 |
| 2007/0275767 A1* | 11/2007 | Steele | H04M 19/04 455/567 |
| 2010/0175028 A1 | 7/2010 | Nozaki | |
| 2010/0199203 A1* | 8/2010 | Bauer | A61C 1/0007 433/101 |
| 2011/0001605 A1* | 1/2011 | Kiani | G16H 40/67 235/492 |
| 2011/0140896 A1* | 6/2011 | Menzel | A61B 5/746 340/573.1 |
| 2011/0229839 A1 | 9/2011 | Yamashita et al. | |
| 2014/0085082 A1* | 3/2014 | Lyon | G16H 40/63 340/539.12 |
| 2016/0067010 A1 | 3/2016 | Nam et al. | |
| 2016/0128647 A1* | 5/2016 | King | A61B 5/7445 715/764 |
| 2016/0287190 A1* | 10/2016 | Park | G16H 15/00 |
| 2017/0102846 A1* | 4/2017 | Ebler | A61M 1/14 |
| 2017/0367759 A1 | 12/2017 | Brannan et al. | |
| 2018/0165991 A1 | 6/2018 | Piras et al. | |
| 2018/0307797 A1 | 10/2018 | St. Louis et al. | |
| 2018/0357384 A1* | 12/2018 | St. Louis | A61G 15/02 |

FOREIGN PATENT DOCUMENTS

| | | | |
|---|---|---|---|
| EP | 3391867 A1 * | 10/2018 | ............ A61G 15/02 |
| JP | H4-336063 | 11/1992 | |
| JP | 2002-011025 | 1/2002 | |
| JP | 2005-144194 | 6/2005 | |
| JP | 2010-075625 | 4/2010 | |
| JP | 2010-516359 | 5/2010 | |
| JP | 2010-157190 | 7/2010 | |
| JP | 2011-189037 | 9/2011 | |
| JP | 2011-193907 | 10/2011 | |
| JP | 2013-231772 | 11/2013 | |
| JP | 2014-502448 | 1/2014 | |
| JP | 2016-055173 | 4/2016 | |
| JP | 2016-171926 | 9/2016 | |
| JP | 2016-214496 | 12/2016 | |
| JP | 2017-108938 | 6/2017 | |
| JP | 2017-225818 | 12/2017 | |
| JP | 2018-022533 | 2/2018 | |
| JP | 2018-061690 | 4/2018 | |
| JP | 2018-518223 | 7/2018 | |
| WO | 2008/089939 | 7/2008 | |
| WO | 2012/064604 | 5/2012 | |

OTHER PUBLICATIONS

Agency for Healthcare Research and Quality, Alert Fatigue, available at https://psnet.ahrq.gov/primer/alert-fatigue (Sep. 7, 2019) (Year: 2019).*
Three Mile Island Special Inquiry Group, U.S. Nuclear Regulatory Commission, Human Factors Evaluation of Control Room Design and Operator Performance at Three Mile Island-2 , available at https://www.osti.gov/servlets/purl/5603680 (Jan. 1980) (Year: 1980).*
Extended Search Report in corresponding European Application No. 21151636.4, dated Jun. 10, 2021.
Stryker, "Sonopet iQ Instruction Manual", Aug. 2019, p. 22-p. 23.
Stryker, "ProCare Services for Sonopet iQ", Internet URL: https://www.stryker.com/content/dam/stryker/nav-nse/products/sonopet-iq/resources/D0000010129%20Rev.%20AA%20Sonopet%20iQ%20ProCare1.pdf, 2019.
Notification of Information Provision issued in Japanese Patent Application No. P2020-005838 dated Apr. 12, 2022 (with English full translation).
Notice of Allowance issued in Japanese Patent Application No. P2020-005839, dated Mar. 7, 2023 (with English partial translation).
Allowed claims filed on Japanese Patent Application No. P2020-005839 (with English partial translation).
Notice of Allowance issued in European Patent Application No. 21151636.4, dated Feb. 16, 2023.

* cited by examiner

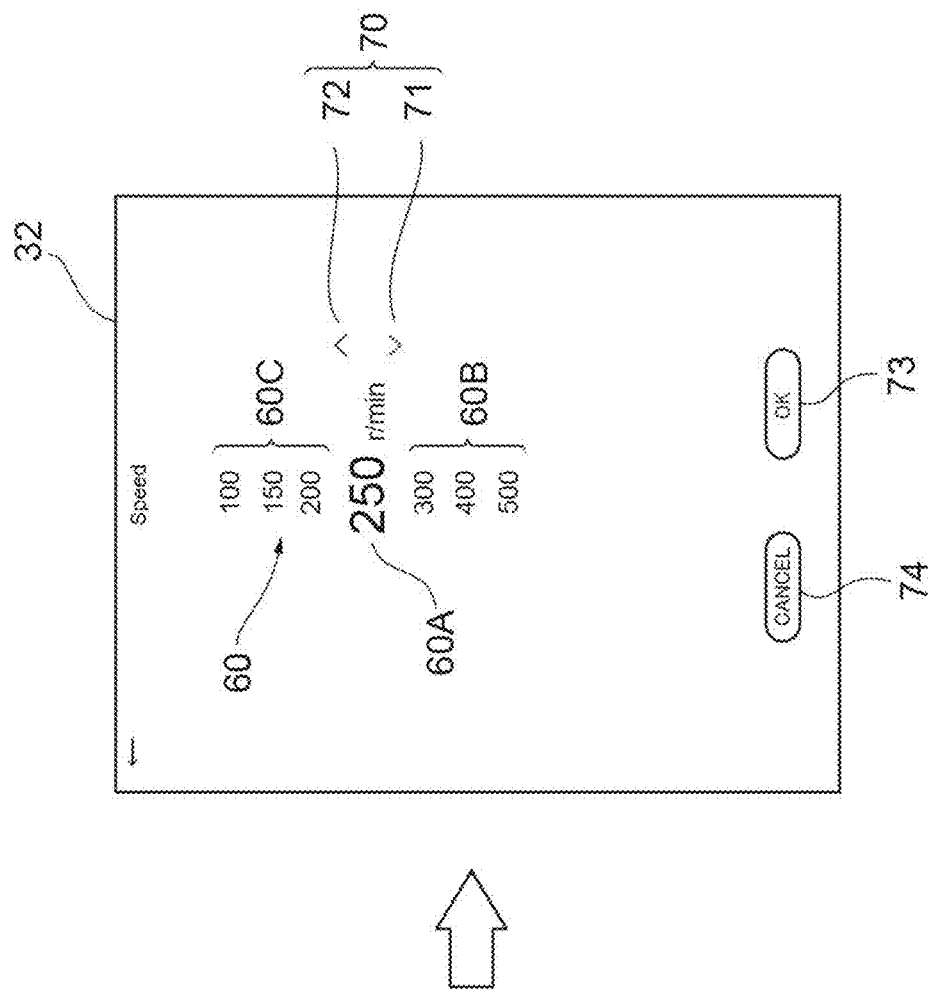
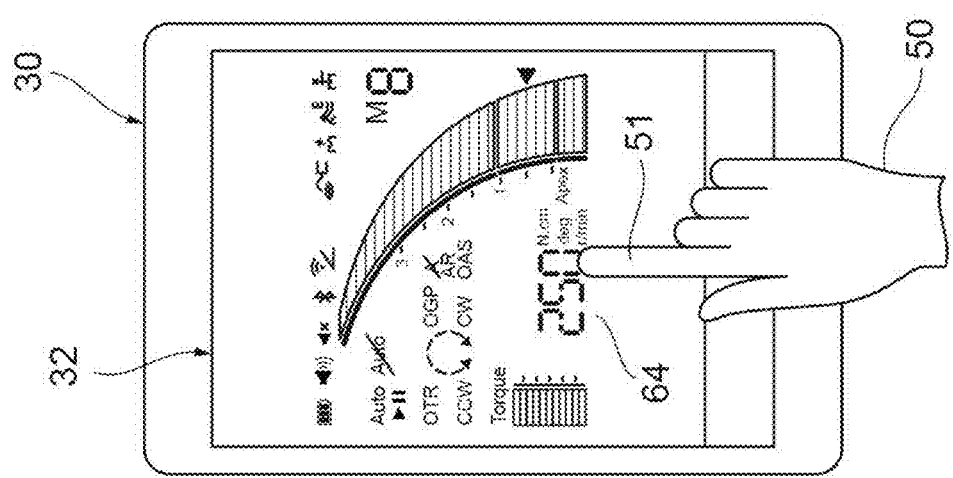

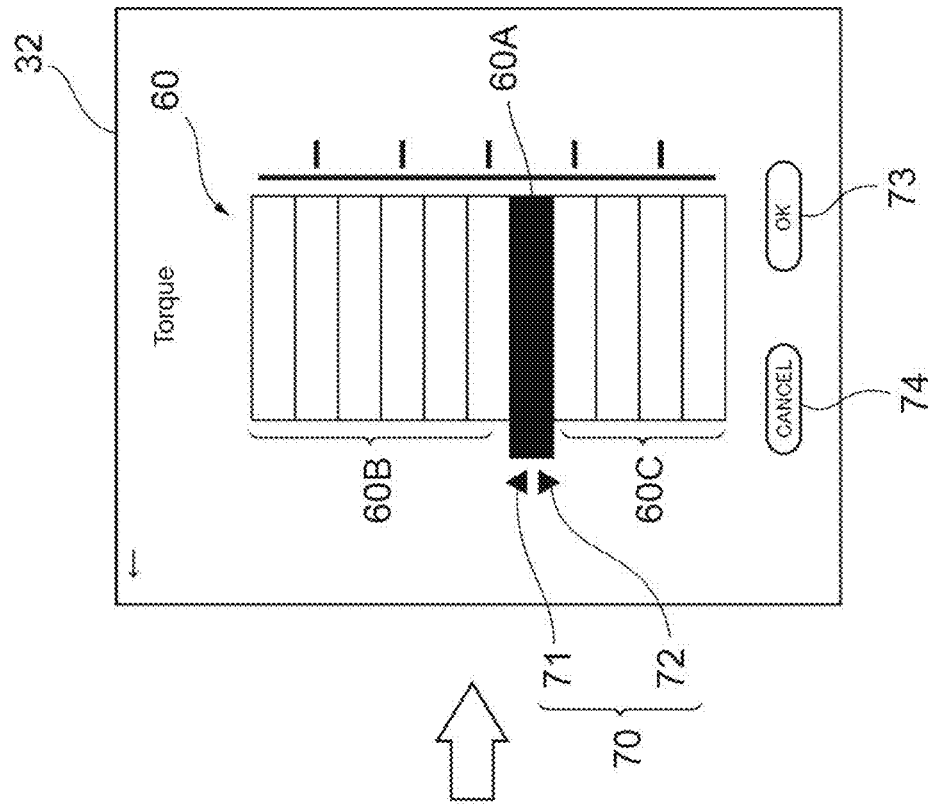
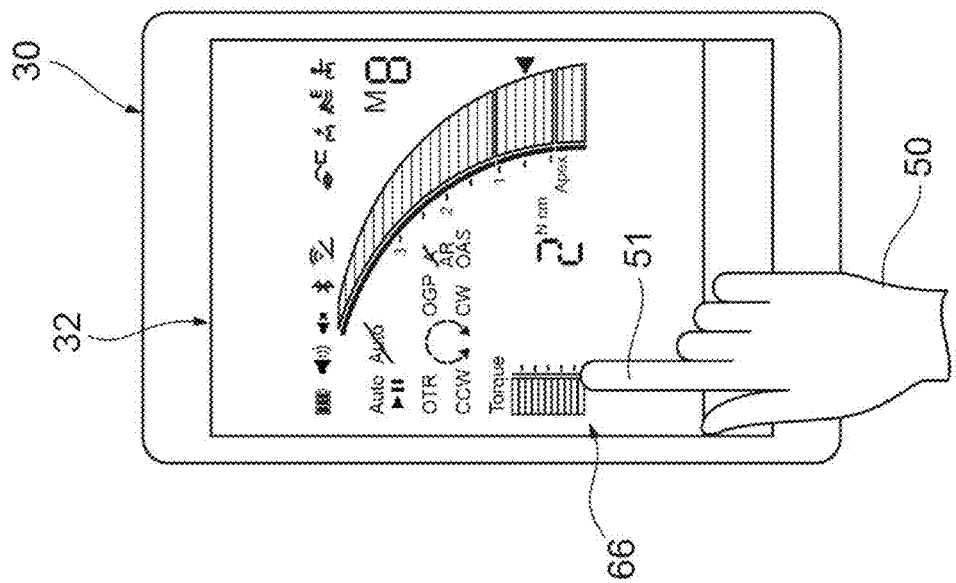

REMOTE CONTROL DEVICE FOR MEDICAL SYSTEM

CROSS-REFERENCE TO RELATED APPLICATIONS

This application claims the benefit of priority from Japanese Patent Applications No. 2020-005838, filed on Jan. 17, 2020, and No. 2020-005839, filed on Jan. 17, 2020, the entire contents of which are incorporated herein by reference.

BACKGROUND

As described in Japanese Unexamined Patent Publication No. 2018-518223 and Japanese Unexamined Patent Publication No. 2011-189037, a medical system using a remote control device that communicates with a medical device is known. Japanese Unexamined Patent Publication No. 2018-518223 describes an endodontic treatment system including a wireless handpiece to which an endodontic treatment tool is attached, a measurement unit, and a calculation display unit capable of communicating with the wireless handpiece. The calculation display unit generates and displays a curve showing the transition of torque in the endodontic treatment tool measured by the measurement unit. Japanese Unexamined Patent Publication No. 2011-189037 describes a treatment device, such as a handpiece for root canal enlargement. A diagnostic function that the treatment device itself does not have is entrusted to an external diagnostic device, and the treatment device is configured to receive and display diagnostic information from the external diagnostic device.

As described in Japanese Unexamined Patent Publication No. 2018-518223 and Japanese Unexamined Patent Publication No. 2016-214496, a system capable of operating a medical device using a touch panel display is known. For example, the endodontic treatment system described in Japanese Unexamined Patent Publication No. 2018-518223 includes a handpiece and a calculation display unit capable of communicating with the handpiece. The calculation display unit is a touch screen type tablet computer or the like. A dentist can program data relevant to dental treatments (data relevant to a set of files, data relevant to the order of files, or data relevant to treatments already given to patients) by himself or herself in the calculation display unit. The medical system described in Japanese Unexamined Patent Publication No. 2016-214496 includes a medical device and a terminal device, such as a smartphone for operating the medical device. The terminal device has a display function and an operation function equal to or higher than those of the medical device.

SUMMARY

When a medical device communicates with a remote control device, display control or the like similar to that in the medical device may be performed in the remote control device. For example, mirroring control having the same (or approximately the same) display contents may be performed in a display unit (display) of the medical device and a display unit (display) of the remote control device. However, when the user is informed of important information, such as a warning on the medical treatment, in a similar manner by the medical device and the remote control device, the user can trust both the medical device and the remote control device. When a situation in which communication between the medical device and the remote control device is not good (for example, communication delay or communication failure) occurs, accurate notification may not be provided in the remote control device. In such a case, an unexpected trouble in the medical treatment may occur.

The disclosure will describe a medical system, a computer program, and a warning notification method that can appropriately notify a user of a warning.

An example medical system including a medical device and a remote control device capable of communicating with the medical device. In the medical system, the medical device includes: a first communication unit that transmits data relevant to medical treatment performed in the medical device to the remote control device; a first display unit that displays a figure or a character corresponding to the data; and a first control unit that may cause the first display unit to display the figure or the character corresponding to the data and that, when the data satisfies conditions for notification of a warning, may cause the medical device to notify of the warning in at least one of visual, auditory, and tactile notification modes. The remote control device includes: a second communication unit that receives the data from the medical device; a second display unit that displays the figure or the character corresponding to the data; and a second control unit that may cause the second display unit to display the figure or the character corresponding to the data and that, when the data satisfies the conditions, may cause the remote control device to notify of the warning only in some of the notification modes performed in the medical device or does not cause the remote control device to notify of the warning.

In the medical system, in the medical device, when the data satisfies the conditions for warning notification, the medical device is controlled by the first control unit to notify of the warning in at least one of the visual, auditory, and tactile notification modes. On the other hand, in the remote control device, the figure or the character corresponding to the data is displayed on the second display unit. The display contents on the second display unit are basically the same as the display contents on the first display unit of the medical device (there may be a different portion). On the other hand, regarding the warning notification, in the remote control device, the remote control device is controlled by the second control unit to notify of the warning only in some of the notification modes performed in the medical device. Alternatively, in the remote control device, no warning notification is provided. Thus, regarding the warning notification, the remote control device has a more limited degree of notification than the medical device. This means that the notification in the medical device is more reliable for the user. For example, even if a situation in which the communication between the two devices is not good (for example, poor communication such as communication delay or communication failure) occurs, the user refers to the notification in the medical device without depending on the notification in the remote control device. Therefore, the user can be appropriately notified of the warning.

In some examples, the first controller may cause the first display to display the figure or the character corresponding to the data and that, when the data satisfies conditions for notification of a warning, may cause the medical device to emit a first warning including at least one of a visual warning, an auditory warning, and a tactile warning. The second controller may cause the second display to display the figure or the character corresponding to the data and that, when the data satisfies the conditions for notification of the warning, may cause the remote control device to emit a second warning that is different than the first warning. In some examples, the medical system may be configured to operate in a plurality of notification modes including a first notification mode and a second notification mode. The second controller may cause the remote control device to emit the second warning in response to receiving the data when the medical system is operating in the first notification mode. The second controller may cause the remote control device to suppress the second warning in response to receiving the data when the medical system is operating in the second notification mode, even when the data satisfies the conditions for notification of the warning.

The medical device may include a sound output unit that notifies of the warning in the auditory notification mode. The first control unit may cause the sound output unit to notify of the warning when the data satisfies the conditions. The second control unit may not cause the remote control device to notify of the warning in the auditory notification mode regardless of whether or not the data satisfies the conditions. In this case, auditory notification (notification by sound) is provided only in the medical device, and is not provided in the remote control device. The second control unit may suppress the second warning in response to receiving the data when the remote control device is operating in the second notification mode, even when the data satisfies the conditions for notification of the warning. By differentiating the two devices by the presence or absence of sound in this manner, it becomes easier for the user to understand the timing at which the warning is issued or the fact of the warning.

The first control unit may not accept a mute setting for the sound output unit, and may perform control so that the sound output unit always emits a predetermined volume. In this case, even if the user mistakenly tries to mute the medical device, the mute setting is not accepted. Since the notification of the warning by sound is provided only in the medical device, it is important to maintain the volume in the sound output unit of the medical device. The notification of the warning by sound in the medical device is reliably transmitted to the user, so that the reliability of the system is improved.

When the data satisfies the conditions, the first control unit may cause the first display unit to display a specific figure or a specific character corresponding to the warning to notify of the warning in the visual notification mode. When the data satisfies the conditions, the second control unit may cause the second display unit to display the specific figure or the specific character to notify of the warning in the visual notification mode. In this case, regarding the visual warning notification, in both the medical device and the remote control device, the specific figure or the specific character is similarly displayed on each display unit. When the communication is good, the user can be notified of the warning at a desired timing by both the medical device and the remote control device. In some examples, the plurality of notification modes may additionally include a third notification mode. The first controller may cause the first display to display the visual warning in the third notification mode when the data satisfies the conditions for notification of the warning. The second controller may also cause the second display to display the visual warning in the third notification mode when the data satisfies the conditions for notification of the warning.

When the data satisfies the conditions, the first control unit may cause the first display unit to display a specific figure or a specific character corresponding to the warning to notify of the warning in the visual notification mode. The second control unit may not cause the remote control device to notify of the warning in the visual notification mode regardless of whether or not the data satisfies the conditions. In this case, since no visual warning notification is provided in the remote control device. The second control unit may suppress the second warning in response to receiving the data when the remote control device is operating in the second notification mode, even when the data satisfies the conditions for notification of the warning. The user understands that attention should be paid to the medical device for the warning.

When the data satisfies the conditions, the first control unit may cause the medical device to notify of the warning in the tactile notification mode. The second control unit may not cause the remote control device to notify of the warning in the tactile notification mode regardless of whether or not the data satisfies the conditions. In this case, since no tactile warning notification is provided in the remote control device. The second control unit may suppress the second warning in response to receiving the data when the remote control device is operating in the second notification mode, even when the data satisfies the conditions for notification of the warning. The user understands that attention should be paid to the medical device for the warning.

Another example computer program used in a remote control device capable of communicating with a medical device. The computer program may cause a computer for controlling the remote control device to execute: a display process in which a display unit of the remote control device is made to display a figure or a character corresponding to data relevant to medical treatment received from the medical device; and a notification process in which, when the data satisfies conditions for notification of a warning, the remote control device is made to notify of the warning only in some of visual, auditory, and tactile notification modes performed in the medical device or the remote control device is not made to notify of the warning.

Another example warning notification method in a remote control device capable of communicating with a medical device. The warning notification method includes: a display step in which a display unit of the remote control device is made to display a figure or a character corresponding to data relevant to medical treatment received from the medical device; and a notification step in which, when the data satisfies conditions for notification of a warning, the remote control device is made to notify of the warning only in some of visual, auditory, and tactile notification modes performed in the medical device or the remote control device is not made to notify of the warning.

In the computer program and the warning notification method, regarding the warning notification, in the remote control device, warning notification is provided only in some of the notification modes performed in the medical device. Alternatively, in the remote control device, no warning notification is provided. Thus, regarding the warning notification, the remote control device has a more limited degree of notification than the medical device. This means that the notification in the medical device is more reliable for the user. For example, even if a situation in which the communication between the two devices is not good (for example, poor communication such as communication delay or communication failure) occurs, the user refers to the notification in the medical device without depending on the notification in the remote control device. Therefore, the user can be appropriately notified of the warning.

As described above, when operating a medical device using a touch panel display such as a terminal device, a user such as a dentist or a doctor operates the touch panel display with a hand or a finger. When the user sets a quantitative parameter using the touch panel display, for example, a scroll icon or the like for displaying a numerical value is displayed on the touch panel display. Numerical value setting in the scroll icon is performed by sliding a hand or a finger in contact with a screen, such as a swipe operation. However, depending on the environment in which the touch panel display is used, it may be difficult to perform such an operation.

In the disclosure, a computer program for a touch panel display capable of improving the operability of the touch panel display for a user, a touch panel display control device with the computer program, and an accepting method will be described.

Another example computer program for a touch panel display for operating a medical device. The computer program may cause a computer for controlling the touch panel display to execute: simultaneously displaying a scroll icon and a button icon for a user to set a quantitative parameter for controlling the medical device; when a swipe or flick operation on the scroll icon is detected on the touch panel display, performing a first accepting process for accepting the swipe or flick operation; and when a tap operation on the button icon is detected on the touch panel display, performing a second accepting process for accepting the tap operation.

Another example accepting method for accepting a predetermined operation on a touch panel display for operating a medical device includes: a display step in which a scroll icon and a button icon for a user to set a quantitative parameter for controlling the medical device are simultaneously displayed on the touch panel display; a first accepting step in which, when a swipe or flick operation on the scroll icon is detected on the touch panel display, the swipe or flick operation is accepted; and a second accepting step in which, when a tap operation on the button icon is detected on the touch panel display, the tap operation is accepted.

In the computer program for a touch panel display and the accepting method, the scroll icon and the button icon for the user to set the quantitative parameter are simultaneously displayed on the touch panel display. The user can swipe or flick the scroll icon with his or her hand or finger. In the first accepting process or the first accepting step, a flick operation is accepted to set the quantitative parameter. Depending on the environment in which the touch panel display is used, it may be difficult to perform such an operation. The "environment in which the touch panel display is used" may include an external environment such as temperature or humidity, a state of the user's hand or finger, and an internal environment such as the user's physical condition or preference. For example, when the humidity is high or when the user wears a silicone or rubber glove on his or her hand, the fingertip does not slide easily on the screen. Alternatively, the user may not like the operation of scrolling the scroll icon. In such a case, in the second accepting process or the second accepting step, a tap operation is accepted to set the quantitative parameter. In addition to the operation of sliding a hand or a finger on the screen, the quantitative parameter can be set by the operation of pressing the screen with the hand or the finger. Therefore, the operability of the touch panel display for the user can be improved.

The computer program for a touch panel display described above may cause the computer to further execute a third accepting process for accepting a long press operation when a long press operation on the button icon is detected on the touch panel display. In this case, in the third accepting process, a long press operation is accepted to set the quantitative parameter. As a result, it is possible to display an operation different from the operation based on the tap operation, for example, an operation of scrolling the scroll icon faster. Therefore, the operability of the touch panel display for the user can be further improved.

The button icon may include an increase button and a decrease button disposed adjacent to a side of at least one of a character or a figure indicating a set value included in the scroll icon. In this case, since the scroll icon and the increase button and the decrease button of the button icon are disposed at positions close to each other, the operability is excellent even when the operation method is not familiar or the operation method is switched.

As still another example touch panel display control device including a storage unit that stores any of the above-described computer programs for a touch panel display, a touch panel display, and a computer may be provided. In the touch panel display control device, the operability when setting the quantitative parameter can be improved.

BRIEF DESCRIPTION OF THE DRAWINGS

FIG. 9A is a diagram showing a start-up operation of a setting screen of a first quantitative parameter on a touch panel display, and FIG. 9B is a diagram showing the setting screen of the first quantitative parameter.

FIG. 12A is a diagram showing a start-up operation of a setting screen of a second quantitative parameter on a touch panel display, and FIG. 12B is a diagram showing the setting screen of the second quantitative parameter.

DETAILED DESCRIPTION

In the following description, with reference to the drawings, the same reference numbers are assigned to the same components or to similar components having the same function, and overlapping description is omitted.

First, a dental treatment system (medical system) S according to a first example will be described with reference to FIGS. 1 and 2. The dental treatment system S is, for example, a dental treatment system for enlarging the root canal by cutting the root canal wall of the patient's tooth. The dental treatment system S may include one or more medical devices. The dental treatment system S includes, for example, a root canal length measuring device (medical device) 10 having an instrument 2 that is a treatment tool for performing root canal enlargement. The dental treatment system S further includes a tablet (remote control device) 30 that is used at a position away from the root canal length measuring device 10 and displays the same items and contents as those on a display 12 in the root canal length measuring device 10.

The dental treatment system S may be applied to any dental treatment other than the root canal enlargement. In this specification, the dental treatment is a concept including medical practice and treatment relevant to dentistry.

Figure 2:
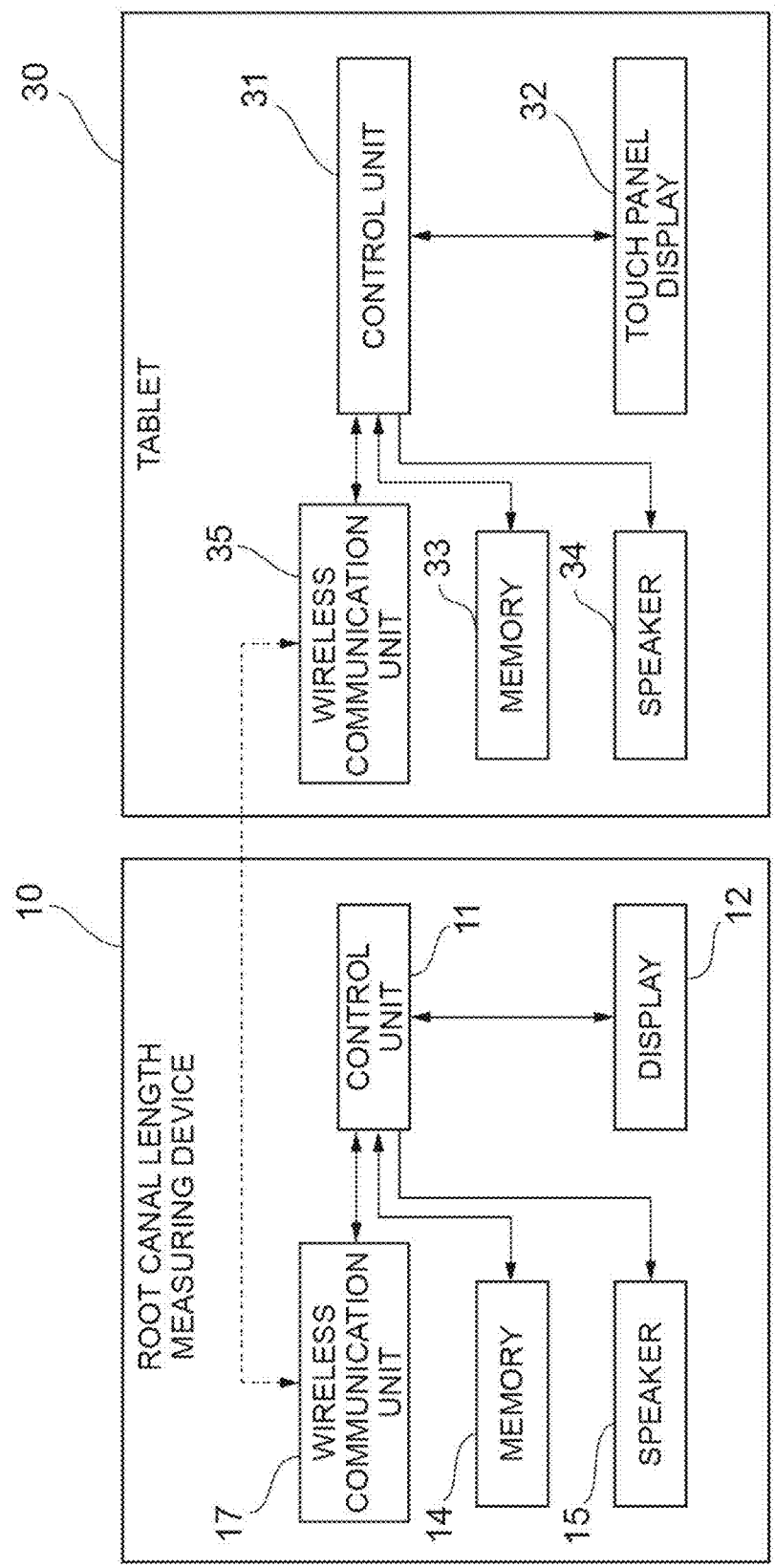
FIG. 2 is a diagram showing the schematic configuration of a medical system including a medical device and a remote control device.

As shown in FIG. 2, the root canal length measuring device 10 is a device used by a dentist as a user to perform root canal treatment. The root canal length measuring device 10 includes a control unit (first control unit) 11, a display (first display unit) 12, a speaker (sound output unit) 15, a memory 14, and a wireless communication unit (first communication unit) 17, and these are housed in the main body (housing). The control unit 11 is a computer including a processor, such as a CPU, and a storage device including a RAM, a ROM, and the like. The control unit 11 controls a motor unit 6 of the instrument 2 based on the control mode, the user setting mode, and the like of a cutting tool 8 input through an operation unit 13. The control unit 11 controls the display of the display 12 based on signals indicating the driving state of the instrument 2 and the treatment state of the tooth. The control unit 11 transmits a signal to the tablet 30 through the wireless communication unit 17 so that the same display items and contents as those displayed on the display 12 are displayed on the tablet 30. So-called mirroring control is performed between the root canal length measuring device 10 and the tablet 30. The "treatment state of the tooth" is a concept including the root canal length described above. The "user" is a concept including not only a dentist who performs dental treatment using the root canal length measuring device 10 but also a dentist other than the dentist, a dental assistant, and the like.

The display 12 includes, for example, a liquid crystal panel, and displays various kinds of information regarding dental treatment in the root canal length measuring device 10. The display 12 displays the driving state of the instrument 2 and the treatment state of the tooth. In the example, the display 12 notifies the user of a warning by displaying the warning when the conditions for warning notification are satisfied in the root canal length measuring device 10. Accordingly, the display 12 notifies the user of the warning in a visual notification mode. In the following description, the "conditions for warning notification in the root canal length measuring device 10" are abbreviated as "warning notification conditions".

The operation unit 13 is a unit that accepts an input from the user for the driving control of the instrument 2. The operation unit 13 is an input device for the user to perform the control mode of the cutting tool 8 that needs to be executed in the treatment or various settings suitable for itself (for example, the number of rotations of the cutting tool 8 or the desired root canal length) or to turn on and off the power.

The speaker 15 emits, for example, an operation sound during setting or a sound corresponding to the root canal length during treatment (including a warning sound when the distal end of the cutting tool 8 reaches the desired root canal length). In the example, the speaker 15 notifies the user of a warning by emitting a sound when the warning notification conditions are satisfied in the root canal length measuring device 10. Accordingly, the speaker 15 notifies the user of the warning in an auditory notification mode. When the warning notification conditions are satisfied, the control unit 11 controls the speaker 15 so that the speaker 15 provides warning notification. The warning notification in this case is provided by emitting a specific sound corresponding to the warning. The specific sound is different from the sound emitted during the normal operation. The specific sound is, for example, a sound that is louder than a sound emitted during the normal operation, a sound that is repeated in a shorter cycle than the sound emitted during the normal operation, or a sound that is emitted in a different pattern.

A computer program for performing warning notification control, which will be described in detail below, is stored in the memory 14. A program for performing various controls of the root canal length measuring device 10 may be stored in the memory 14. In addition, setting information, such as the number of rotations, is stored in the memory 14.

The wireless communication unit 17 transmits data relevant to the medical treatment performed by the root canal length measuring device 10 to the tablet 30. For example, the wireless communication unit 17 transmits data indicating the root canal length to a wireless communication unit 35 of the tablet 30 by wireless communication. In this specification, the "data" corresponds to any "value" relevant to the medical treatment performed by using the root canal length measuring device 10.

Figure 1:
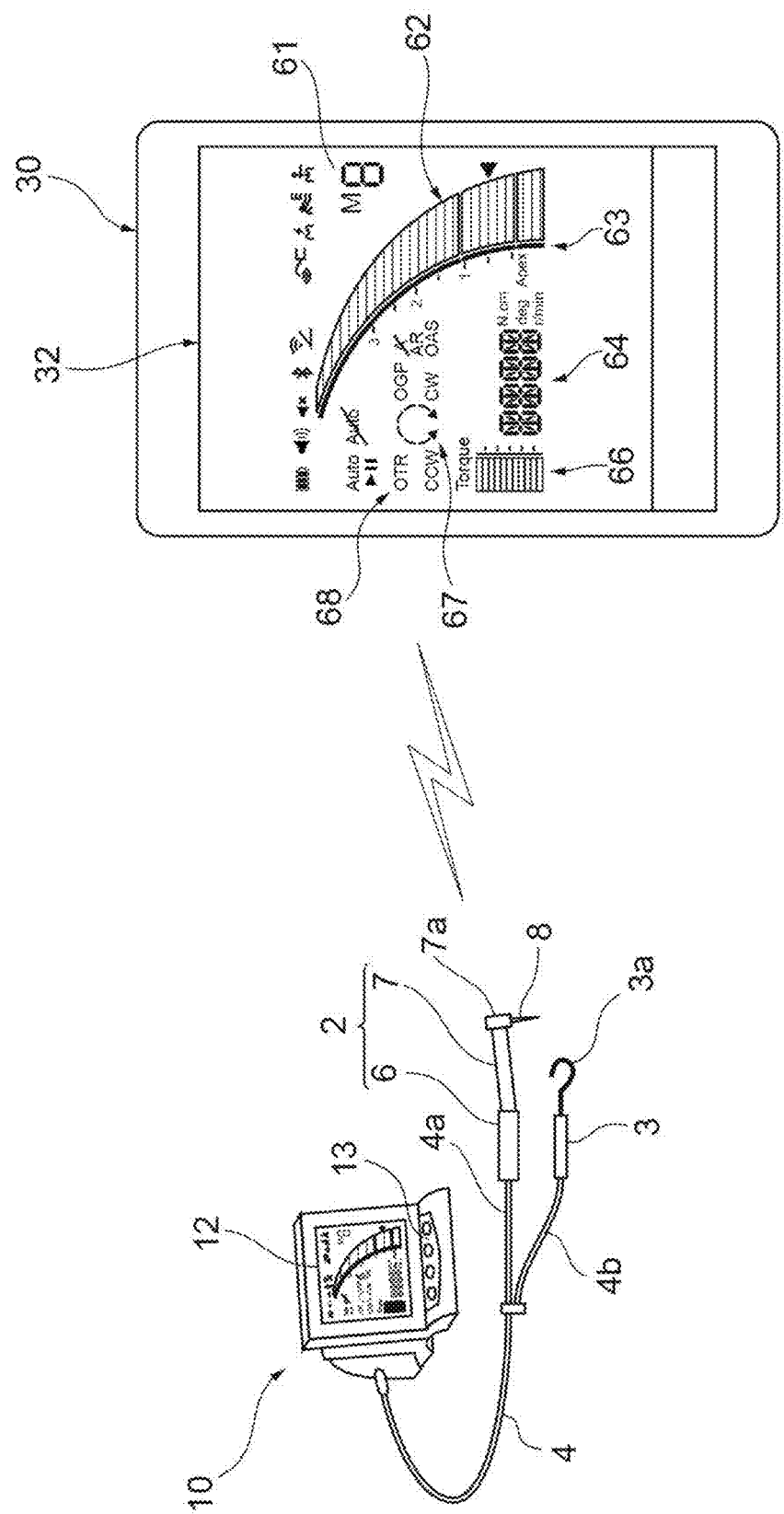
FIG. 1 is a diagram showing a medical system according to a first example of the disclosure.

As shown in FIG. 1, the root canal length measuring device 10 includes an oral electrode 3 connected to an oral electrode cable 4b and the instrument 2 connected to an instrument cable 4a. As shown in FIG. 1, the instrument cable 4a and the oral electrode cable 4b may be provided so as to branch from the middle of one cable 4 connected to the device main body. In the cable 4 (the instrument cable 4a and the oral electrode cable 4b), a power supply lead wire for driving the instrument 2, a signal lead wire for transmitting various signals, and the like are provided.

The instrument 2 includes a handpiece 7 held by the user to enlarge the root canal and the motor unit 6 detachably connected to the proximal end side of the handpiece 7. The handpiece 7 includes a head portion 7a provided at its distal end, and the cutting tool (a file, a reamer, or the like) 8 is held in the head portion 7a. The motor unit 6 has a built-in micromotor for rotationally driving the cutting tool 8 through a rotational force transmission mechanism in the handpiece 7. The cutting tool 8 functions as a first electrode of a root canal length measuring circuit for detecting the root canal length, that is, the position of the distal end of the cutting tool 8 in the root canal. The oral electrode 3 includes a hook portion 3a provided at its distal end. When root canal enlargement is performed, the hook portion 3a is hooked on the corner of the patient' mouth and functions as a second electrode of the root canal length measuring circuit.

The root canal length measuring device 10 measures the root canal length during treatment for the patient. A closed circuit is formed by the cutting tool 8 inserted into the root canal of the tooth and the oral electrode 3 hung on the corner of the patient's mouth. By measuring the impedance between the cutting tool 8 and the oral electrode 3, the distance from the distal end position (root apex) of the tooth to the distal end of the cutting tool 8 is measured. The measured distance is assumed to be the root canal length. For example, the root canal length measuring circuit is formed within the root canal length measuring device 10.

When using the root canal length measuring device 10, the user can set all quantitative parameters by using the operation unit 13. The quantitative parameter is a parameter for controlling each unit of the root canal length measuring device 10, and is, for example, a parameter relevant to the operation of the cutting tool 8 in the instrument 2. In the dental treatment system S, the user can set these quantitative parameters by using the tablet 30 that is a terminal device.

The tablet 30 is a terminal used by the user. As shown in FIG. 2, the tablet 30 includes a control unit (second control unit) 31, a touch panel display (second display unit) 32, a memory 33, a speaker 34, and a wireless communication unit (second communication unit) 35. Since the wireless communication unit 35 is provided, the tablet 30 can wirelessly communicate with the wireless communication unit 17 of the root canal length measuring device 10. The wireless communication between the tablet 30 and the root canal length measuring device 10 may be any known wireless communication means, including, for example, Bluetooth (registered trademark) and Wi-Fi.

Figure 5B:
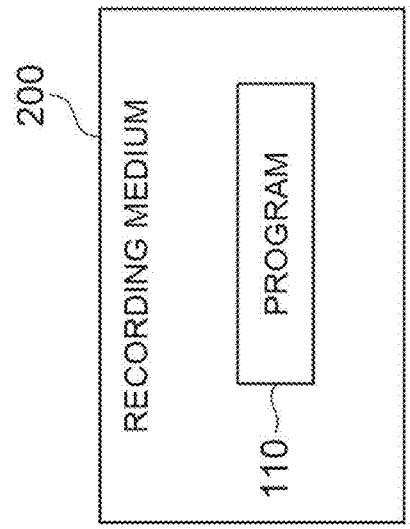
FIG. 5B is a diagram showing a recording medium that stores a computer program.
Figure 5A:
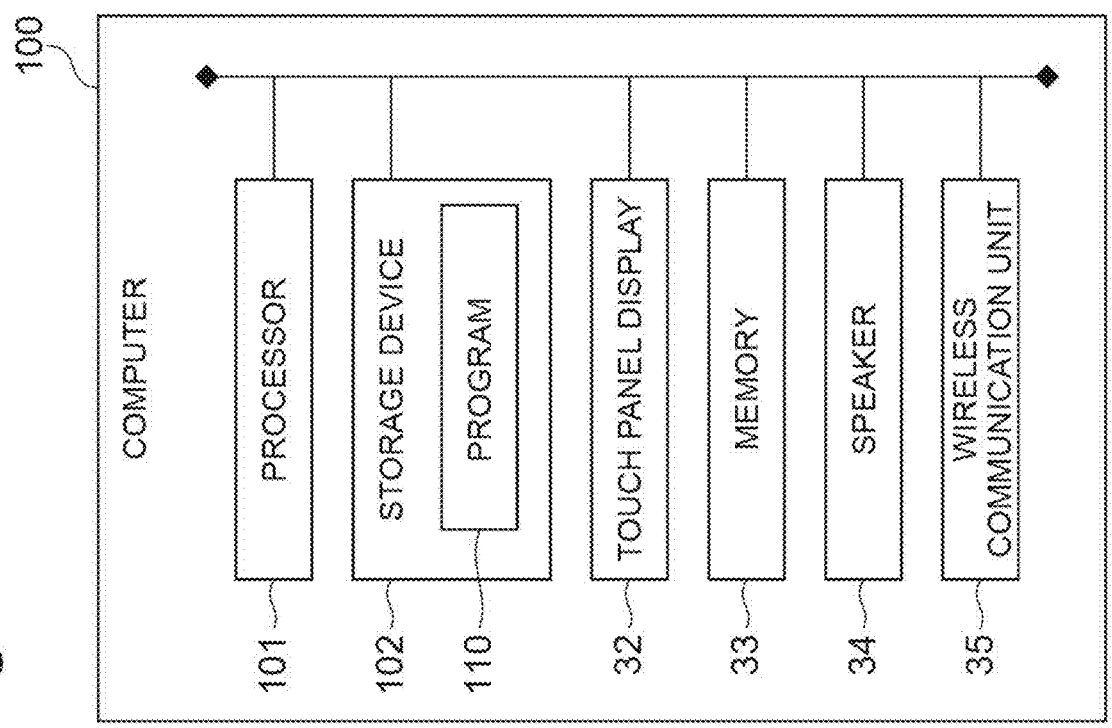
FIG. 5A is a diagram showing an example of the hardware configuration of a computer capable of functioning as a tablet.

As shown in FIG. 5A, a computer 100 that functions as the tablet 30 includes a processor 101 such as a CPU, a storage device 102 including a RAM and a ROM, the touch panel display 32, the memory 33, the speaker 34, and the wireless communication unit 35. The control unit 31 includes, for example, the processor 101 and the storage device 102, and controls the touch panel display 32. By transmitting a signal to the root canal length measuring device 10 based on a set value of the quantitative parameter input by the user, the control unit 31 controls the root canal length measuring device 10 so that the root canal length measuring device 10 operates according to the set value. The control unit 11 of the root canal length measuring device 10 receives the signal indicating the set value of the quantitative parameter, which is transmitted from the tablet 30, and controls each unit of the root canal length measuring device 10. The control unit 11 controls the instrument 2 based on the control mode, the user setting mode, and the like of the instrument 2 input through the operation unit. The control unit 11 controls the display of the display 12 based on signals indicating the driving state of the instrument 2 and the treatment state of the tooth. By visually checking the touch panel display 32, the user can check whether or not the situation of treatment is appropriate or check whether or not the desired treatment state is realized.

The comparison (common points and differences) of the notification modes between the root canal length measuring device 10 and the tablet 30 will be described. In this specification, the "notification modes" can include visual notification, auditory notification, and tactile notification. The visual notification is, for example, a display on the display 12 and the touch panel display 32. The auditory notification is, for example, the output of sound in the speaker 15 and the speaker 34. The tactile notification is, for example, the generation of vibration by a vibrator (not shown) provided in the root canal length measuring device 10 and the tablet 30. Each notification mode is not limited to the above mode, and other known modes may be adopted.

The control unit 31 of the tablet 30 receives a signal transmitted from the root canal length measuring device 10 and performs mirroring control to control the display of the touch panel display 32. By the mirroring control, the same display items and contents as those displayed on the display 12 of the root canal length measuring device 10 are displayed on the tablet 30. Accordingly, the display 12 of the root canal length measuring device 10 displays a figure or a character corresponding to data relevant to the medical treatment. On the other hand, the touch panel display 32 of the tablet 30 displays a figure or a character corresponding to data relevant to the medical treatment basically similarly to the display 12.

In order to realize mirroring control on the display 12 and the touch panel display 32, the control unit 11 of the root canal length measuring device 10 may cause the display 12 to display a figure or a character corresponding to data relevant to the medical treatment. The control unit 31 of the tablet 30 may cause the touch panel display 32 to display a figure or a character corresponding to data relevant to the medical treatment basically similarly to the control unit 11. By these controls, the display contents on the display 12 and the display contents on the touch panel display 32 are the same or approximately the same.

Figure 4B:
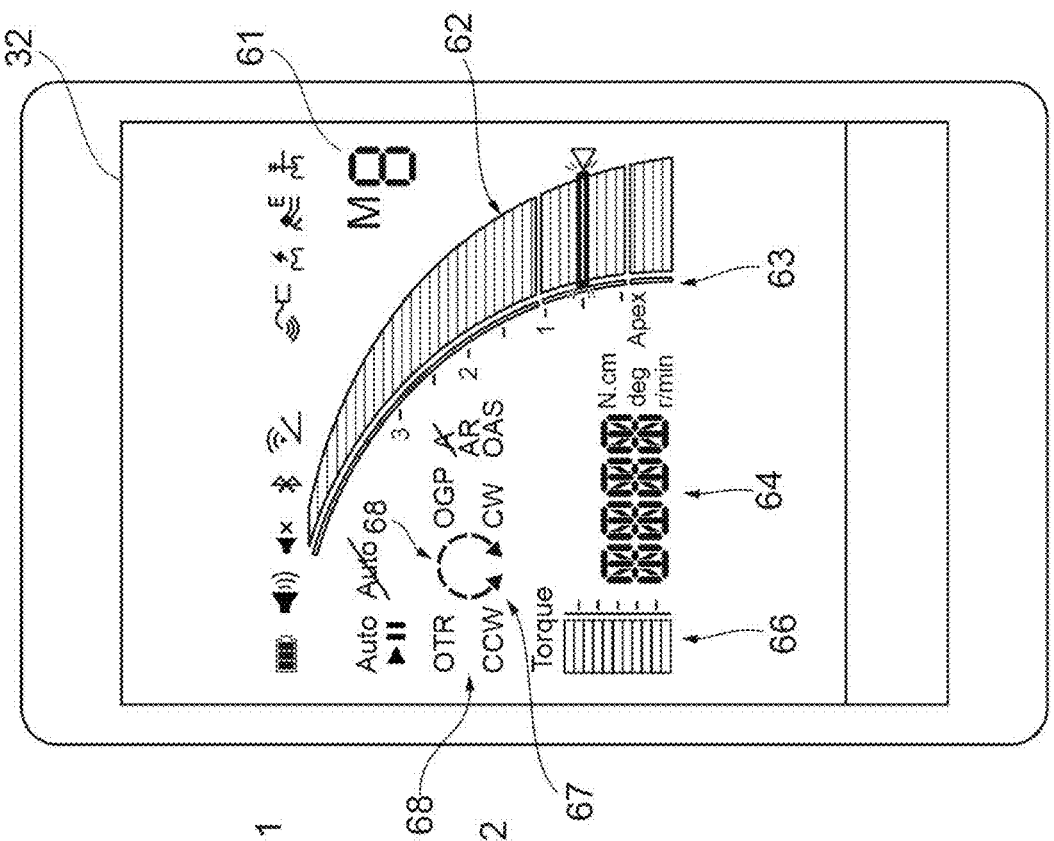
FIG. 4B is a diagram showing an example of a warning notification mode in a remote control device in the case of FIG. 4A.
Figure 4A:
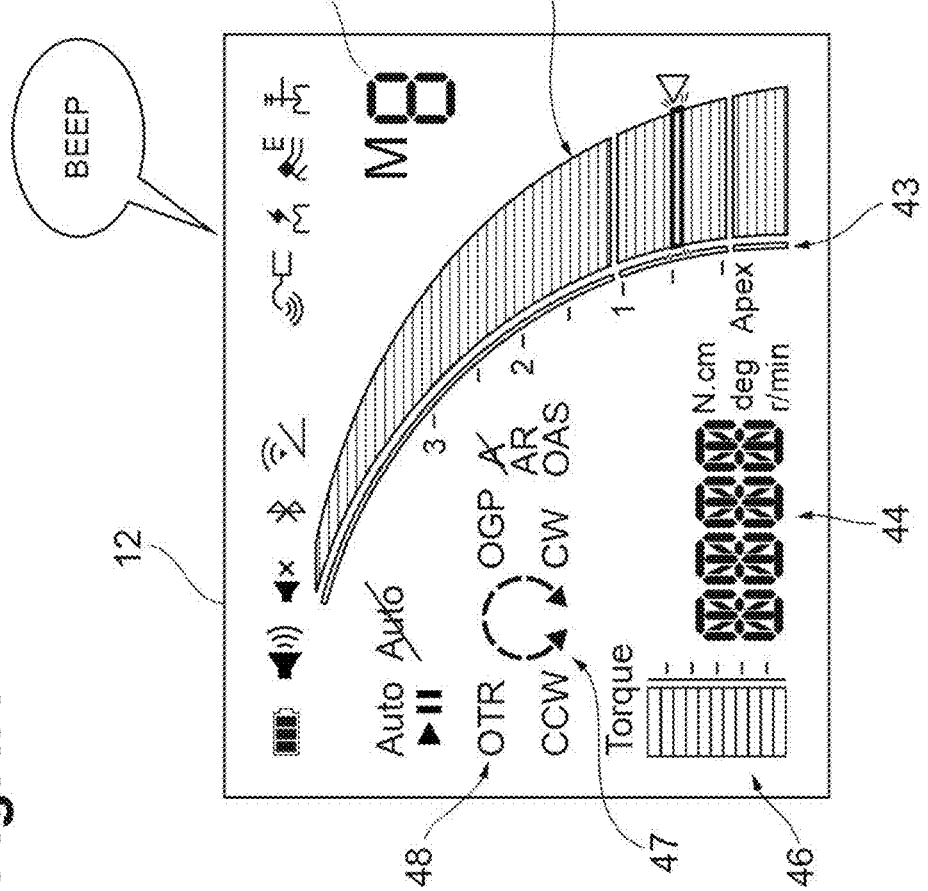
FIG. 4A is a diagram showing an example of a warning notification mode in a medical device.

As shown in FIG. 4A, an operation mode display portion 41 for displaying a setting mode selected by the user, a dot display portion 42 including a large number of elements for displaying the measured root canal length in detail, a zone display portion 43 for displaying the root canal length in a stepwise manner by dividing the root canal length into a plurality of zones, a numerical display portion 44 for displaying the number of rotations of the cutting tool 8 and the like, and a dot display portion 46 including a large number of elements for displaying the value of torque applied to the cutting tool 8 are provided on the display 12 of the root canal length measuring device 10. A control mode character notation 48 and a control mode FIG. 47 for indicating the control mode being executed are provided on the display 12.

In the example, the display 12 notifies the user of a warning by displaying the warning when the warning notification conditions are satisfied in the root canal length measuring device 10. Accordingly, the display 12 notifies the user of a warning in a visual notification mode. The visual notification mode means, for example, displaying a specific figure or a specific character in response to a predetermined warning. When the data relevant to the medical treatment satisfies the warning notification conditions, the control unit 11 may cause the display 12 to display a specific figure or a specific character to provide warning notification in a visual notification mode.

As shown in FIG. 1, an operation mode display portion 61 for displaying a setting mode selected by the user, a dot display portion 62 including a large number of elements for displaying the measured root canal length in detail, a zone display portion 63 for displaying the root canal length in a stepwise manner by dividing the root canal length into a plurality of zones, a numerical display portion 64 for displaying the number of rotations of the cutting tool 8 and the like, and a dot display portion 66 including a large number of elements for displaying the value of torque applied to the cutting tool 8 are provided on the touch panel display 32 of the tablet 30. A control mode character notation 68 and a control mode FIG. 67 for indicating the control mode being executed are provided on the touch panel display 32.

In the example, the touch panel display 32 notifies the user of a warning by displaying the warning when the warning notification conditions are satisfied in the root canal length measuring device 10. Accordingly, the touch panel display 32 notifies the user of a warning in a visual notification mode. When the data relevant to the medical treatment satisfies the warning notification conditions, the control unit 31 may cause the touch panel display 32 to display a specific figure or a specific character to provide warning notification in a visual notification mode. The specific figure and the specific character displayed on the touch panel display 32 are the same as or approximately the same as the specific figure and the specific character displayed on the display 12 for the same warning notification conditions.

Referring back to FIG. 2, the speaker 34 outputs a sound necessary for medical treatment to the user during normal operation of the root canal length measuring device 10. The wireless communication unit 35 receives the data relevant to the medical treatment transmitted from the wireless communication unit 17 of the root canal length measuring device 10. The "normal operation" refers to an operation that does not include a state/status for which a warning is to be given.

Subsequently, quantitative parameters set in the dental treatment system S will be described. The quantitative parameters include a volume in the speaker of the root canal length measuring device 10. The quantitative parameters may include the number of rotations of the end motor in the root canal cutting enlargement, or may include the torque value of the cutting tool 8. The quantitative parameters may include the length (position) of the root canal to automatically stop (auto-stop) the cutting tool 8 or the length (position) of the root canal to automatically reverse (apically reverse) the cutting tool 8. The quantitative parameters may include the length (position) of the root canal for warning, which is for notifying the user of a warning when the distal end of the cutting tool 8 is located at a predetermined root canal length (position). The quantitative parameters may include the amount of LED light of the display 12 in the root canal length measuring device 10.

The memory 33 of the tablet 30 stores a computer program 110 for performing warning notification control to be described in detail below. The computer program 110 is, for example, an application program. The memory 33 stores setting information regarding the various quantitative parameters described above. The memory 33 may store other computer programs for performing various controls of the root canal length measuring device 10. Instead of the memory 33, the ROM (storage device 102) of the control unit 31 may be used.

The control unit 31 (computer 100 shown in FIG. 5A) executes an operating system and a computer program. Each functional element (each process) of the tablet 30 is realized by causing the control unit 31 or the memory 33 to read the computer program 110 and execute the computer program 110. The computer program 110 includes codes for realizing each functional element of the tablet 30. The control unit 31 may cause the touch panel display 32 and the wireless communication unit 35 to operate according to the computer program 110 to perform reading and writing of data in the memory 33 or the like. By this processing, each functional element of the tablet 30 is realized. The data or database required for processing may be stored in the memory 33 or the like. As shown in FIG. 5B, the computer program 110 may be provided after being fixedly recorded on a tangible recording medium 200, such as a CD-ROM, a DVD-ROM, or a semiconductor memory. Alternatively, the computer program 110 may be provided through a communication network as a data signal superimposed on a carrier wave.

In the dental treatment system S, during the normal operation, there is no particular difference between the display control of the display 12 and the display control of the touch panel display 32 and no particular difference between the sound output control of the speaker 15 and the sound output control of the speaker 34. In the example, the control unit 11 and the control unit 31 store the warning notification conditions in medical treatment. For example, among the quantitative parameters described above, the "length of the root canal for warning" is one of the warning notification conditions. Other examples of the warning notification conditions include "abnormal root canal length measuring circuit (situation in which the root canal length cannot be measured correctly)", "torque applied to the motor", "the number of rotations of the motor", and "remaining battery level (battery voltage)". The control unit 11 and the control unit 31 store the same determination condition regarding whether or not to provide warning notification, and make a determination by performing a predetermined calculation or the like based on the acquired data and the determination condition. The determination condition is, for example, a threshold value regarding the value shown in the data. The threshold value may be a threshold value to be compared with the value itself, or may be a threshold value to be compared with a value converted by a predetermined arithmetic expression. When it is determined that a warning is to be given, the control unit 11 and the control unit 31 process the root canal length measuring device 10 and the tablet 30 in different methods.

Figure 3:
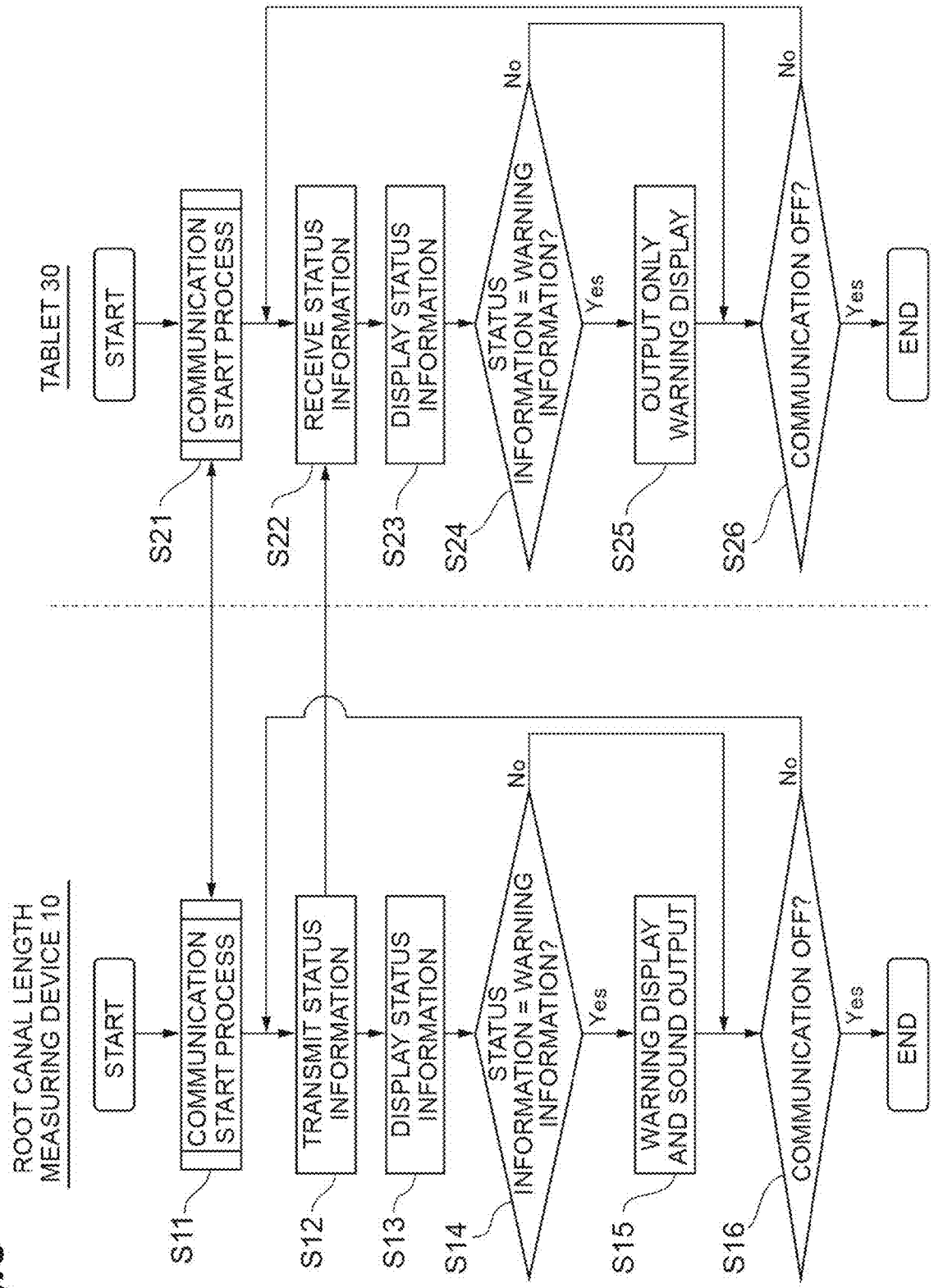
FIG. 3 is a flowchart showing a process performed by each control unit of a medical device and a remote control device.

Next, processes performed by the control unit 11 of the root canal length measuring device 10 and the control unit 31 of the tablet 30 will be described with reference to FIG. 3. First, the control unit 11 starts a process for communication with the tablet 30 through the wireless communication unit 17 (step S11). The control unit 31 starts a process for communication with the root canal length measuring device 10 through the wireless communication unit 35 (step S21). Then, the control unit 11 transmits data relevant to the medical treatment performed in the root canal length measuring device 10 to the tablet 30 (step S12). The control unit 31 receives the data relevant to the medical treatment transmitted from the control unit 11 (step S22). In the example shown in FIG. 3, as an example of the data relevant to the medical treatment, "status information" is exemplified. The status information may be, for example, the root canal length in the root canal enlargement, the number of rotations, the torque, or the rotation direction.

The control unit 11 controls the display 12 to display the status information of the root canal length measuring device 10 (step S13). The control unit 31 controls the touch panel display 32 to display the status information of the root canal length measuring device 10 (step S23; display process/display step). As a result, the mirroring control described above is realized. As shown in FIG. 1, the display screens of the display 12 and the touch panel display 32 include similar figures and characters. In this manner, the control unit 11 may cause the display 12 to display a figure or a character corresponding to the data relevant to the medical treatment. The control unit 31 may cause the touch panel display 32 to display a figure or a character corresponding to the data relevant to the medical treatment. A dentist who performs medical treatment using the root canal length measuring device 10 may refer to the display 12 or the tablet 30. A user other than the dentist can grasp the status or state of the treatment performed by the dentist by referring to the tablet 30.

Then, the control unit 11 determines whether or not the status information corresponds to information to be warned (step S14). The control unit 11 makes a determination by performing a predetermined calculation or the like based on the value shown in the status information and the stored warning notification conditions. For example, when the value of the "length of the root canal for warning" is stored as the warning notification conditions, the control unit 11 compares the current root canal length shown in the status information with the "length of the root canal for warning". When the current root canal length is equal to or greater than the value of the "length of the root canal for warning", the status information corresponds to the information to be warned. On the other hand, the control unit 31 determines whether or not the status information corresponds to the information to be warned (step S24). The control unit 31 makes a determination by performing a predetermined calculation or the like based on the value shown in the status information and the stored warning notification conditions. The determination process in the control unit 31 may be the same as the determination process in the control unit 11.

When it is determined that the status information corresponds to the information to be warned (step S14; YES), the control unit 11 controls the display 12 and the speaker 15 to output a warning display on the display 12 and a warning sound from the speaker 15 (step S15). For example, as shown in FIG. 4A, the display 12 includes the dot display portion 42, which is a gauge configured to include a plurality of bars indicating the level. On the display 12, one bar of the gauge of the dot display portion 42 blinks to be highlighted. At the same time, a warning sound, such as "beep", is output from the speaker 15. The blinking of the bar corresponds to a specific figure.

When it is determined that the status information corresponds to the information to be warned (step S24; YES), the control unit 31 controls only the touch panel display 32 to output only the warning display on the touch panel display 32 (step S25; notification process/notification step). For example, as shown in FIG. 4B, on the touch panel display 32, one bar of the dot display portion 62 blinks to be highlighted. However, unlike the display 12, no warning sound is output from the speaker 34. The blinking of the bar corresponds to a specific figure.

As described above, in the dental treatment system S, when the data relevant to the medical treatment satisfies the warning notification conditions, the control unit 11 of the root canal length measuring device 10 may cause the root canal length measuring device 10 to provide warning notification in two notification modes for visual notification and auditory notification. On the other hand, when the data relevant to the medical treatment satisfies the warning notification conditions, the control unit 31 of the tablet 30 may cause the tablet 30 to provide warning notification in a notification mode for only visual notification. The control unit 31 may cause the tablet 30 to provide warning notification only in some of the notification modes (only the warning display) performed in the root canal length measuring device 10.

As described above, in the example, the output of the warning sound in the root canal length measuring device 10 is important. In the root canal length measuring device 10, the sound of the speaker 15 cannot be muted (cannot be set to 0). The user can adjust the volume of the speaker 15 by using the operation unit 13 or the like of the root canal length measuring device 10, but the control unit 11 does not accept a mute setting for the speaker 15. The control unit 11 controls the speaker 15 so that the speaker 15 can always emit a predetermined volume. On the other hand, on the touch panel display 32 of the tablet 30, a message (character), a figure, or the like indicating that a mute operation on the speaker 15 is invalid is displayed. Examples of the message include "volume off setting is not possible in the root canal length measuring device for safe treatment".

Each of these steps S11 to S15 and S21 to S25 may be executed at regular intervals, for example, every few milliseconds, and the stored status information may be overwritten each time each step is executed.

After the warning output process of step S15, the control unit 11 determines whether or not the communication has ended or has been interrupted (step S16). When it is determined that the communication has ended or has been interrupted (step S16; YES), a series of processes end. When it is determined in step S16 that the communication continues (step S16; NO), the control unit 11 returns to the process of step S12. After the warning output process of step S25, the control unit 31 determines whether or not the communication has ended or has been interrupted (step S26). When it is determined that the communication has ended or has been interrupted (step S26; YES), a series of processes end. When it is determined in step S26 that the communication continues (step S26; NO), the control unit 31 returns to the process of step S22.

When it is determined in step S14 that the status information does not correspond to the information to be warned (step S14; NO), the control unit 11 performs the determination process of step S16. When it is determined in step S24 that the status information does not correspond to the information to be warned (step S24; NO), the control unit 31 performs the determination process of step S26.

Through the above series of processes, the transmission and reception of the status information in the root canal length measuring device 10 and the tablet 30, the mirroring control of the touch panel display 32, and the warning notification when the warning notification conditions are satisfied are performed.

In the dental treatment system S of the example, The dental treatment system S is configured to operate in a second notification mode. When the data satisfies the warning notification conditions in the root canal length measuring device 10, the root canal length measuring device 10 is controlled by the control unit 11 to provide warning notification (a first warning) in both the notification modes for visual notification and auditory notification. On the other hand, in the tablet 30, a figure or a character corresponding to the data is displayed on the touch panel display 32. The display contents on the touch panel display 32 are basically the same as the display contents on the display 12 of the root canal length measuring device 10 (there may be a different portion). On the other hand, regarding the warning notification, in the tablet 30, the tablet 30 is controlled by the control unit 31 to provide warning notification (a second warning) only in some of the notification modes (warning display) performed in the root canal length measuring device 10. Thus, regarding the warning notification, the tablet 30 has a more limited degree of notification than the root canal length measuring device 10. This means that the notification in the root canal length measuring device 10 is more reliable for the user. For example, even if a situation in which the communication between the two devices is not good (for example, poor communication such as communication delay or communication failure) occurs, the user refers to the notification in the root canal length measuring device 10 without depending on the notification in the tablet 30. Therefore, the user can be appropriately notified of the warning. If the user depends on the notification in the tablet 30, a trouble in the medical treatment may occur in the case of poor communication. According to the dental treatment system S of the disclosure, such a trouble in the medical treatment can be prevented in advance.

A computer program and a warning notification method of the example can also obtain the same operational effects as those in the dental treatment system S described above.

In the auditory notification mode, the control unit 31 does not cause the tablet 30 to provide warning notification regardless of whether or not the data satisfies the warning notification conditions. The control unit 31 may suppress the second warning. The control unit 31 may suppress or prohibit the auditory warning. Accordingly, auditory notification (notification by sound) is provided only in the root canal length measuring device 10, and is not provided in the tablet 30. By differentiating the two devices by the presence or absence of sound in this manner, it becomes easier for the user to understand the timing at which the warning is issued or the fact of the warning.

The control unit 11 does not accept a mute setting for the speaker 15, and performs control so that the speaker 15 can always emit a predetermined volume. Even if the user mistakenly tries to mute the root canal length measuring device 10, the mute setting is not accepted. Since the notification of a warning by sound is provided only in the root canal length measuring device 10, it is important to maintain the volume in the speaker 15 of the root canal length measuring device 10. The notification of a warning by sound in the root canal length measuring device 10 is reliably transmitted to the user, so that the reliability of the system is improved.

When the data satisfies the warning notification conditions, the control unit 11 may cause the display 12 to display a specific figure or a specific character corresponding to the warning to provide warning notification in a visual notification mode. When the data satisfies the warning notification conditions, the control unit 31 may cause the touch panel display 32 to display a specific figure or a specific character to provide warning notification in a visual notification mode. Regarding the visual warning notification, in both the root canal length measuring device 10 and the tablet 30, a specific figure or a specific character is similarly displayed on each display unit (same warning). The dental treatment system S is configured to operate in a third notification mode. When the communication is good, the user can be notified of the warning at a desired timing by both the root canal length measuring device 10 and the tablet 30.

It is to be understood that not all aspects, advantages and features described herein may necessarily be achieved by, or included in, any one particular example. Indeed, having described and illustrated various examples herein, it should be apparent that other examples may be modified in arrangement and detail. The dental treatment system S may be configured to operate in a first notification mode. In the first notification mode, the second warning in the tablet 30 may be different than the first warning in the root canal length measuring device 10.

When the data satisfies the warning notification conditions, the control unit 11 may cause the display 12 (first display unit) to display a specific figure or a specific character corresponding to the warning to provide warning notification in a visual notification mode. On the other hand, unlike in the above example, the control unit 31 may not cause the tablet 30 (remote control device) to provide warning notification in the visual notification mode regardless of whether or not the data satisfies the warning notification conditions. The control unit 31 may suppress the second warning. The control unit 31 may suppress or prohibit the visual warning. In this case, since no visual warning notification is provided in the tablet 30, the user understands that attention should be paid to the root canal length measuring device 10 for the warning. In this case, the tablet 30 may be used by the user specially for, for example, normal medical treatment state checking or various settings of the medical device.

In the example described above, the case where the visual notification and the auditory notification are used has been mainly described. However, the invention is not limited thereto, and a tactile notification may be appropriately combined. In medical devices, one to three of the three types of notifications may be adopted. In the remote control device, warning notification may be provided only in some of the notification modes (a smaller number of notification modes than the one to three notification modes) performed in the medical device. The second control unit of the remote control device may be configured so as not to cause the remote control device to provide warning notification.

When the data satisfies the warning notification conditions, the control unit 11 may cause the root canal length measuring device 10 (medical device) to provide warning notification in a tactile notification mode, such as vibration. In contrast, regardless of whether or not the data satisfies the warning notification conditions, the control unit 31 may not cause the tablet 30 (remote control device) to provide warning notification in the tactile notification mode. The control unit 31 may suppress the second warning. The control unit 31 may suppress or prohibit the tactile warning. In this case, since no tactile warning notification is provided in the tablet 30, the user understands that attention should be paid to the root canal length measuring device 10 for the warning. In this case, the tablet 30 may be used by the user specially for, for example, normal medical treatment state checking or various settings of the medical device.

When providing visual warning notification, the specific figure is not limited to blinking and any form may be adopted. Various display modes, such as an enlarged display, a display that changes colors, a display with movement, and a display that combines a figure and a character, may be adopted. It is desirable that the display mode is easily visible to the user. When providing visual warning notification, only a specific character may be used. Examples of the specific character include a character enlarged from a normal character, a character with a different color, and a character indicating a warning message, and various display modes may be adopted for the character.

The invention may be applied to any medical device and medical system other than dental treatment. The invention can be applied to any system as long as this is a medical system including a medical device and a remote control device each having a display unit.

Figure 6:
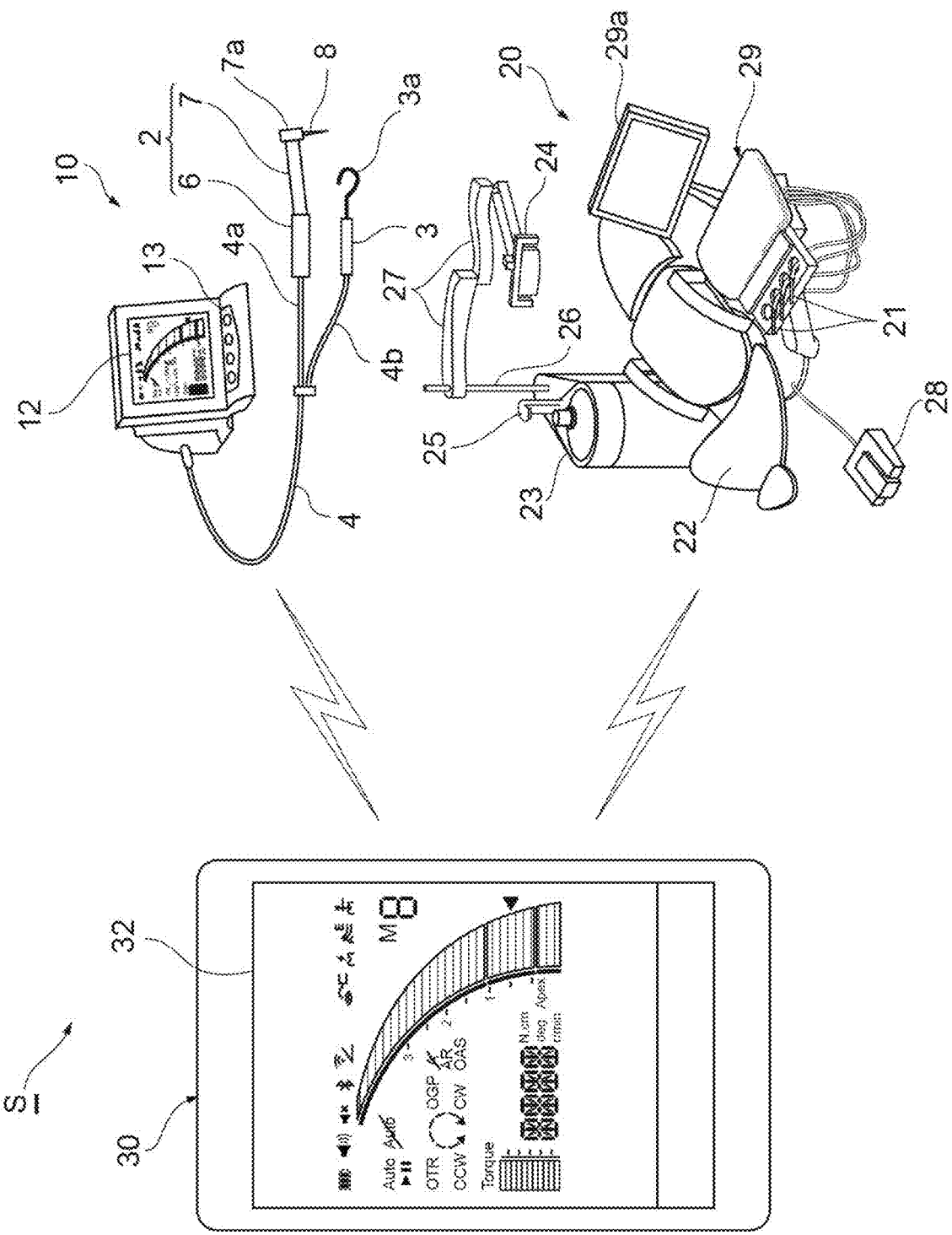
FIG. 6 is a diagram showing a medical system to which a touch panel display control device according to a second example of the disclosure is applied.
Figure 7:
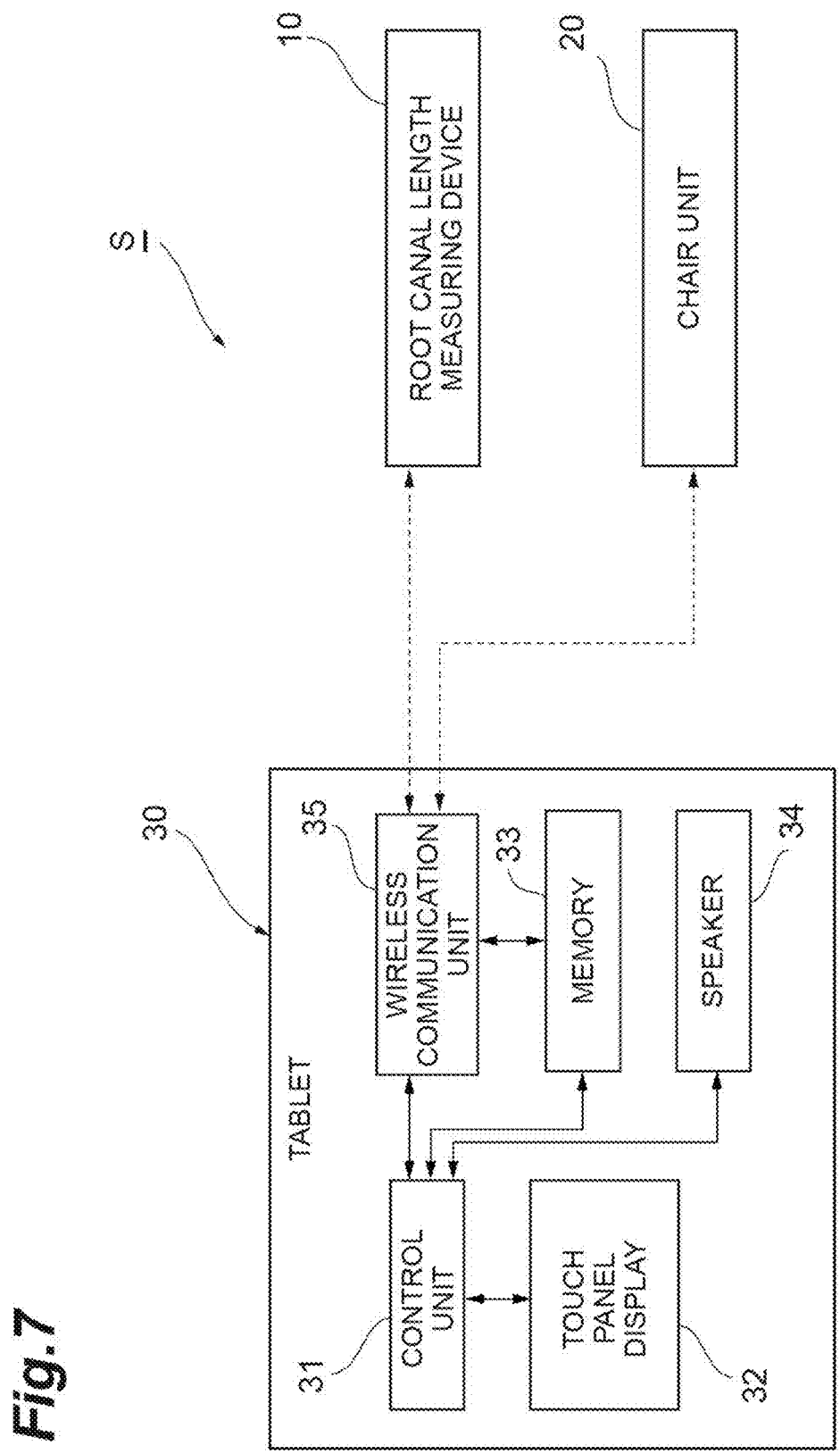
FIG. 7 is a diagram showing the schematic configuration of a root canal treatment system including a tablet, a root canal length measuring device, and a chair unit.

Next, a dental treatment system (medical system) S to which a tablet (touch panel display control device) 30 according to a second example is applied will be described with reference to FIGS. 6 and 7. The dental treatment system S is, for example, a dental treatment system for enlarging the root canal by cutting the root canal wall of the patient's tooth. The dental treatment system S may include one or more medical devices. The dental treatment system S includes, for example, a small root canal length measuring device (medical device) 10 having an instrument 2, which is a treatment tool for performing root canal enlargement, and a chair unit (medical device) 20 having a plurality of instruments 21, which are treatment tools for performing root canal enlargement for a patient on a medical table 22. The dental treatment system S further includes a tablet 30 that is used at a position away from the root canal length measuring device 10, for example, in a tray table 29 provided in the chair unit 20 and that displays the same items and contents as those on a display 12 and a monitor 29a in the root canal length measuring device 10 and the chair unit 20.

The dental treatment system S may be applied to any dental treatment other than the root canal enlargement. In this specification, the dental treatment is a concept including medical practice and treatment relevant to dentistry.

The root canal length measuring device 10 has an operation unit 13 that accepts an input from the user for the driving control of the instrument 2. The root canal length measuring device 10 displays various kinds of information regarding dental treatment on the display 12. The operation unit 13 and the display 12 can be used to set the driving mode of the instrument 2. The display 12 displays the driving state of the instrument 2 and the treatment state of the tooth. In this specification, the "user" is a concept including not only a dentist who performs dental treatment using the root canal length measuring device 10 or the chair unit 20 but also another dentist other than the dentist, a dental assistant, and the like. In addition to the above, the configuration and usage of the root canal length measuring device 10 and the instrument 2 are the same as those in the first example, and accordingly the description thereof will be omitted.

The chair unit 20 is a device that is used by a dentist as a user to perform dental treatment on a patient (not shown). The chair unit 20 may be used by a dentist to perform root canal treatment, similarly to the root canal length measuring device 10. The chair unit 20 includes the medical table 22 that supports a patient, a spittoon 23 that is provided on the side of the medical table 22 so that the patient rinses his or her mouth, a surgical light 24 that is placed above the medical table 22 to illuminate the patient's oral cavity, and a foot pedal 28 that is operated by the user to drive the medical table 22 and the like.

Equipment, such as a water tap 25, is attached to the spittoon 23. The surgical light 24 is supported by a support column 26 provided upright on the side of the medical table 22 and the water tap 25 and a plurality of arm portions 27 connected to the support column 26. When the user grips and moves a side portion of the surgical light 24, the plurality of arm portions 27 move freely, so that the surgical light 24 can be stopped at a predetermined position. The foot pedal 28 is electrically connected to a driving mechanism in the medical table 22. The chair unit 20 further includes the tray table 29 disposed near the side of the user. Articles relevant to dental treatment are placed on the horizontal placing surface of the tray table 29. A plurality of instruments 21 having the same tools as the cutting tool 8 are held in a front portion (a portion facing the user) of the tray table 29. The monitor 29a is provided in a rear portion of the tray table 29 (a portion on a side opposite to the user).

The tray table 29 has, for example, the operation unit 13 that is provided on the front surface of the tray table 29 to accept an input from the user for the driving control of the instrument 21. The chair unit 20 displays various kinds of information regarding dental treatment on the monitor 29a.

The tray table 29 including the monitor 29a can be used to set the driving mode of the instrument 21. The monitor 29a displays the driving state of the instrument 21 and the treatment state of the tooth.

When the user uses the root canal length measuring device 10 or the chair unit 20, the user can set any quantitative parameter using the operation unit 13 of the root canal length measuring device 10 or the tray table 29 (monitor 29a) of the chair unit 20. The quantitative parameter is a parameter for controlling each unit of the root canal length measuring device 10 and the chair unit 20, and is, for example, a parameter relevant to the operations of the instrument 2 and the cutting tool 8 in the instrument 21. In the dental treatment system S, the user can set these quantitative parameters by using the tablet 30 that is a terminal device.

The tablet 30 is a terminal used by the user. As shown in FIG. 7, the tablet 30 includes a control unit 31, a touch panel display 32, a memory 33, a speaker 34, and a wireless communication unit 35. Since the wireless communication unit 35 is provided, the tablet 30 can wirelessly communicate with each wireless communication unit (not shown) of the root canal length measuring device 10 and the chair unit 20. The wireless communication between the tablet 30 and each of the root canal length measuring device 10 and the chair unit 20 may be any known wireless communication means, including, for example, Bluetooth (registered trademark) and Wi-Fi. In addition, wired communication may be performed between the tablet 30 and each of the root canal length measuring device 10 and the chair unit 20.

The control unit 31 is a computer including a processor, such as a CPU, and a storage device including a RAM, a ROM, and the like. The control unit 31 controls the touch panel display 32. The control unit 31 transmits a signal to the root canal length measuring device 10 or the chair unit 20 based on a set value of the quantitative parameter input by the user, so that the root canal length measuring device 10 or the chair unit 20 operates according to the set value. Each of the root canal length measuring device 10 and the chair unit 20 includes a control unit that receives a signal indicating the set value of the quantitative parameter, which is transmitted from the tablet 30, and controls each unit of the root canal length measuring device 10 and the chair unit 20. These control units control the instruments 2 and 21, respectively, based on the control mode, the user setting mode, and the like of the instruments 2 and 21 input through the operation unit. The control units control the display 12 and the monitor 29a, respectively, based on the signals indicating the driving states of the instruments 2 and 21 and the treatment state of the tooth. By visually checking the touch panel display 32, the user can check whether or not the situation of treatment is appropriate or check whether or not the desired treatment state is realized.

The control unit 31 of the tablet 30 receives a signal transmitted from the root canal length measuring device 10 or the chair unit 20 and performs mirroring control to control the display of the touch panel display 32. By the mirroring control, the same display items and contents as those displayed on the display 12 of the root canal length measuring device 10 or the monitor 29a of the chair unit 20 are displayed on the tablet 30. The touch panel display 32 of the tablet 30 may have the same function as the operation unit 13 of the root canal length measuring device 10 or the operation unit of the chair unit 20.

Figure 8:
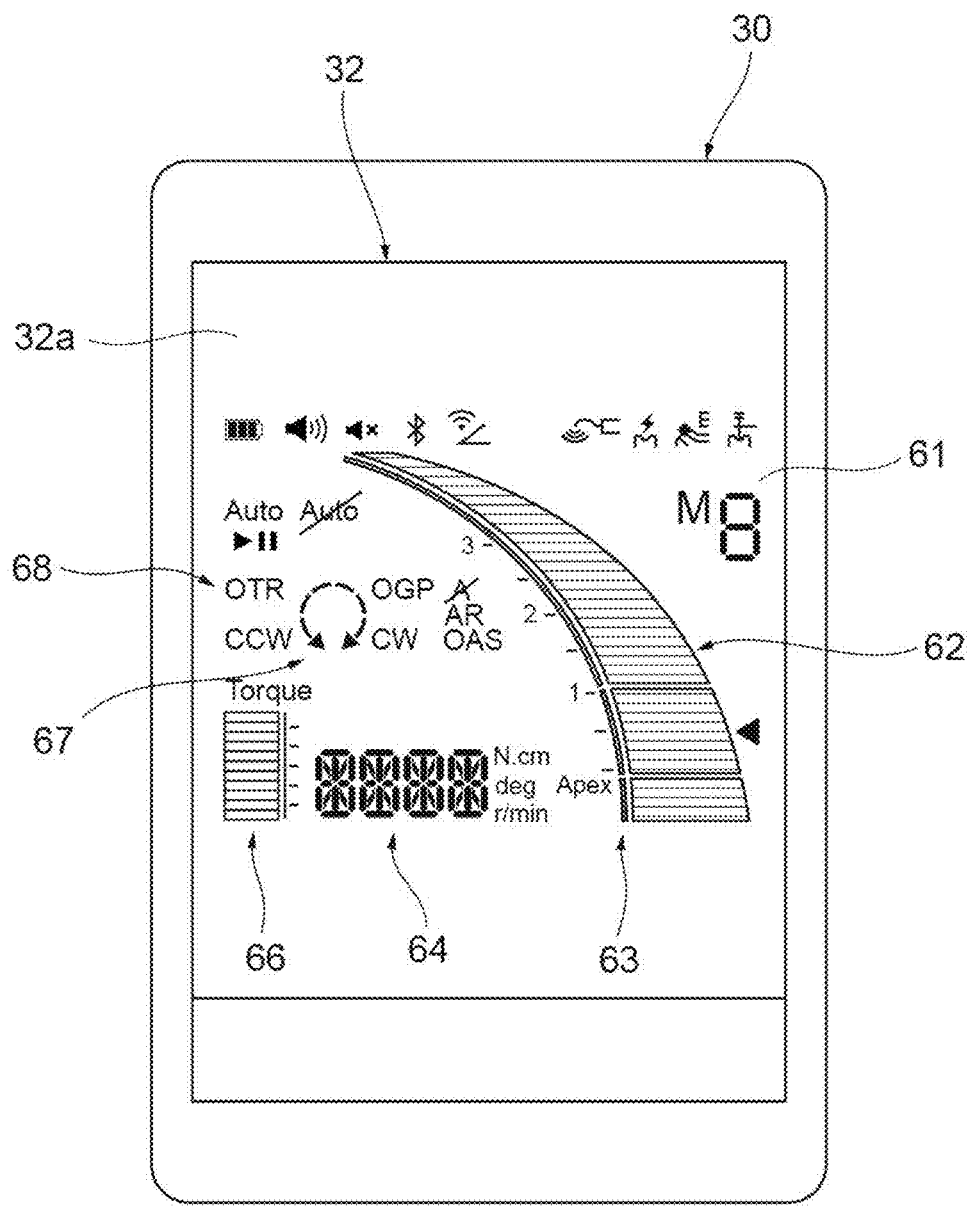
FIG. 8 is a diagram showing a touch panel display of a tablet.

Subsequently, the touch panel display 32 of the tablet 30 will be described with reference to FIG. 8. The touch panel display 32 has a screen 32a including a surface capable of accepting an input from the user. When the user's hand or finger or the like touches the screen 32a, an input with respect to a character or a figure displayed on the screen 32a (specifically, various operations such as swipe, flick, tap, and long press) becomes possible according to the touch. The detection method in the touch panel display 32 is not particularly limited, and may be a known method including a capacitance method, a resistance method, and an infrared method. The display device of the touch panel display 32 may include a liquid crystal display or an organic EL display.

By the mirroring control, the same display as on the display 12 and the monitor 29a is performed on the touch panel display 32 of the tablet 30. An operation mode display portion 61 for displaying a setting mode selected by the user, a dot display portion 62 including a large number of elements for displaying the measured root canal length in detail, a zone display portion 63 for displaying the root canal length in a stepwise manner by dividing the root canal length into a plurality of zones, a numerical display portion 64 for displaying the number of rotations of the cutting tool 8 and the like, and a dot display portion 66 including a large number of elements for displaying the value of torque applied to the cutting tool 8 are provided on the touch panel display 32. A control mode character notation 68 and a control mode FIG. 67 for indicating the control mode being executed are provided on the touch panel display 32.

Subsequently, quantitative parameters set in the dental treatment system S will be described. The quantitative parameters include a volume in the speaker of a medical device, such as the root canal length measuring device 10 or the chair unit 20. The quantitative parameters may include the number of rotations of the end motor in the root canal cutting enlargement, or may include the torque value of the cutting tool 8. The quantitative parameters may include the length (position) of the root canal to automatically stop (auto-stop) the cutting tool 8 or the length (position) of the root canal to automatically reverse (apically reverse) the cutting tool 8. The quantitative parameters may include the amount of LED light of the display 12 or the monitor 29a in a medical device, such as the root canal length measuring device 10 or the chair unit 20.

Figure 10:
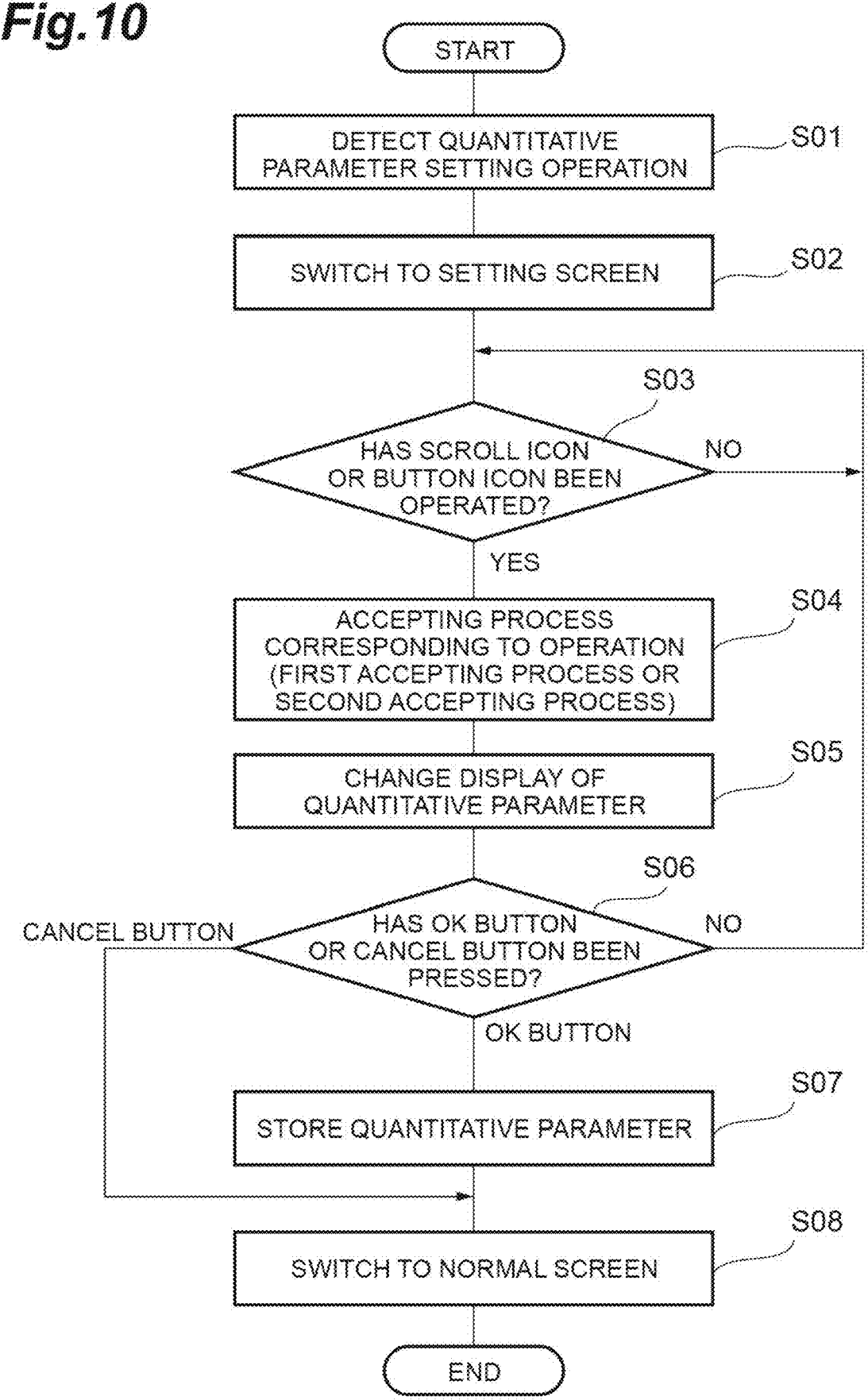
FIG. 10 is a flowchart showing a process performed by a control unit of a tablet.

Subsequently, a computer program for the touch panel display 32 and an accepting method for accepting a predetermined operation on the touch panel display 32 in the example will be described with reference to FIGS. 9, 10, and 11. The memory 33 of the tablet 30 stores a computer program for controlling the touch panel display 32 to be described in detail below. The computer program is, for example, an application program. The memory 33 stores setting information regarding the various quantitative parameters described above. The memory 33 may store other computer programs for performing various controls of the root canal length measuring device 10 and the chair unit 20. Instead of the memory 33, the ROM of the control unit 31 may be used. The tablet 30 and the computer program according to the second example have the same configuration as the configuration shown in FIG. 5A (or FIG. 5B).

The control unit 31 executes an operating system and a computer program. Each functional element (each process) of the tablet 30 is realized by causing the control unit 31 or the memory 33 to read the computer program and execute the computer program. The computer program includes codes for realizing each functional element of the tablet 30. The control unit 31 may cause the touch panel display 32 and the wireless communication unit 35 to operate according to the computer program to perform reading and writing of data in the memory 33 or the like. By this processing, each functional element of the tablet 30 is realized. The data or database required for processing may be stored in the memory 33 or the like. The computer program may be provided after being fixedly recorded on a tangible recording medium, such as a CD-ROM, a DVD-ROM, or a semiconductor memory. Alternatively, the computer program may be provided through a communication network as a data signal superimposed on a carrier wave.

Hereinafter, for some types of quantitative parameters, a setting operation and an accepting process for the setting operation will be described. In the following description, an example in which the root canal length measuring device 10 is operated will be described. FIG. 9A is a diagram showing a start-up operation of a setting screen of a first quantitative parameter on the touch panel display 32, and FIG. 9B is a diagram showing the setting screen of the first quantitative parameter. FIG. 10 is a flowchart showing a process performed by the control unit 31 of the tablet 30. Here, the first quantitative parameter is the number of rotations of the end motor. As shown in FIG. 9A, a finger 51 of a user 50 touches and taps a numerical display portion 64 indicating the number of rotations. As shown in FIG. 10, the control unit 31 detects a quantitative parameter setting operation (step S01). Then, the control unit 31 switches the display of the touch panel display 32 to the quantitative parameter setting screen (step S02). Thus, by tapping a quantitative parameter that needs to be set on the normal screen, the screen is switched and the setting screen of the quantitative parameter is displayed on the touch panel display 32.

As shown in FIG. 9B, in step S02, the control unit 31 simultaneously displays a scroll icon 60 and a button icon 70 for the user to set the number of rotations of the end motor in the root canal length measuring device 10 on the touch panel display 32 (display step). The scroll icon 60 extends in the vertical direction on the screen. The scroll direction of the scroll icon 60 is the vertical direction on the screen. In the example shown in FIG. 9B, the scroll icon 60 is a vertically long (rectangular) region where a numerical value of 100 to 500 r/min is displayed. In a central portion of the scroll icon 60 in the vertical direction, a set value 60A (in the shown example, 250 r/min) is highlighted. Below the set value 60A, one or more larger set value candidates 60B (in the shown example, three set value candidates in units of 100 r/min) are displayed. Above the set value 60A, one or more smaller set value candidates 60C (in the shown example, three set value candidates in units of 50 r/min) are displayed.

The button icon 70 including an increase button 71 and a decrease button 72 is displayed on the side of the scroll icon 60. The "side" is a side in a direction (in the shown example, a left-right direction) perpendicular to the scroll direction of the scroll icon 60. For example, the button icon 70 is disposed on the right side of the scroll icon 60. In the example, the increase button 71 and the decrease button 72 are disposed adjacent to the right side of the character indicating the set value 60A included in the scroll icon 60. The increase button 71 and the decrease button 72 are arrayed in the vertical direction of the screen, and the increase button 71 is disposed below the decrease button 72. An OK button 73 that is pressed when the setting is completed and a cancel button 74 that is pressed when returning to the normal screen are displayed at the bottom of the setting screen.

Figure 11A:
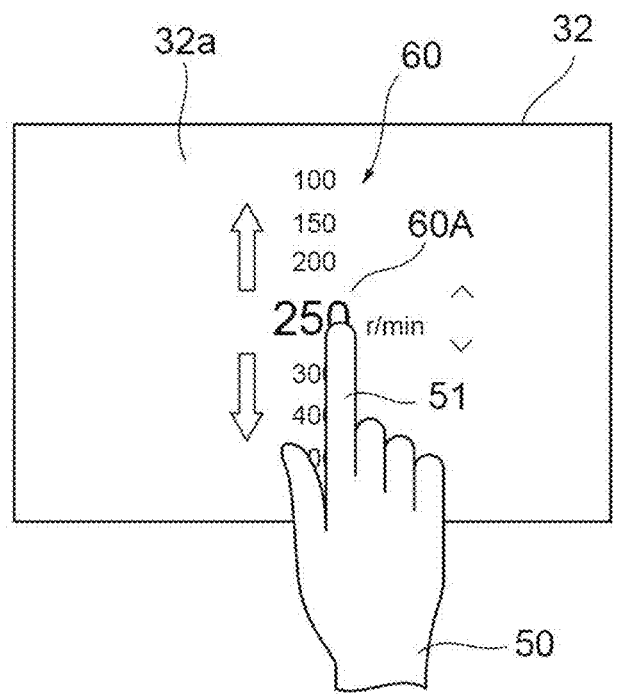
FIG. 11A is a diagram showing a setting example of the first quantitative parameter on the setting screen of FIG. 9B.

Then, the control unit 31 determines whether or not the scroll icon 60 or the button icon 70 has been operated (step S03). For example, as shown in FIG. 11A, the finger 51 of the user 50 touches the set value 60A on the setting screen, and swipes or flicks upward or downward starting from the set value 60A while keeping the finger 51 in contact with the screen 32a. In this case, the control unit 31 detects the movement of the finger 51, determines that the scroll icon 60 has been operated (step S03; YES), and accepts the swipe operation or the flick operation (step S04; first accepting step/first accepting process). The control unit 31 changes the quantitative parameter displayed on the scroll icon 60 (step S05). For example, when it is detected that a swipe operation or a flick operation has been performed upward by the finger 51, the control unit 31 performs display control by scrolling the scroll icon 60 so that the larger set value candidates 60B are sequentially displayed at the position of the set value 60A. When it is detected that a swipe operation or a flick operation has been performed downward by the finger 51, the control unit 31 performs display control by scrolling the scroll icon 60 so that the smaller set value candidates 60C are sequentially displayed at the position of the set value 60A.

In this quantitative parameter change display control, the control unit 31 may make the scroll speeds in the swipe operation and the flick operation different. For example, in the case of a swipe operation, the scroll icon 60 may be scrolled at approximately the same speed as the movement speed of the finger 51, and in the case of a flick operation, the scroll icon 60 may be scrolled at a predetermined speed. In the case of a swipe operation, the control unit 31 may stop the scrolling of the scroll icon 60 when the movement of the finger 51 in contact with the screen 32a is stopped or when the finger 51 is separated from the screen 32a. In the case of a flick operation, the control unit 31 may stop scrolling after a predetermined number of display changes of the scroll icon 60.

Figure 11B:
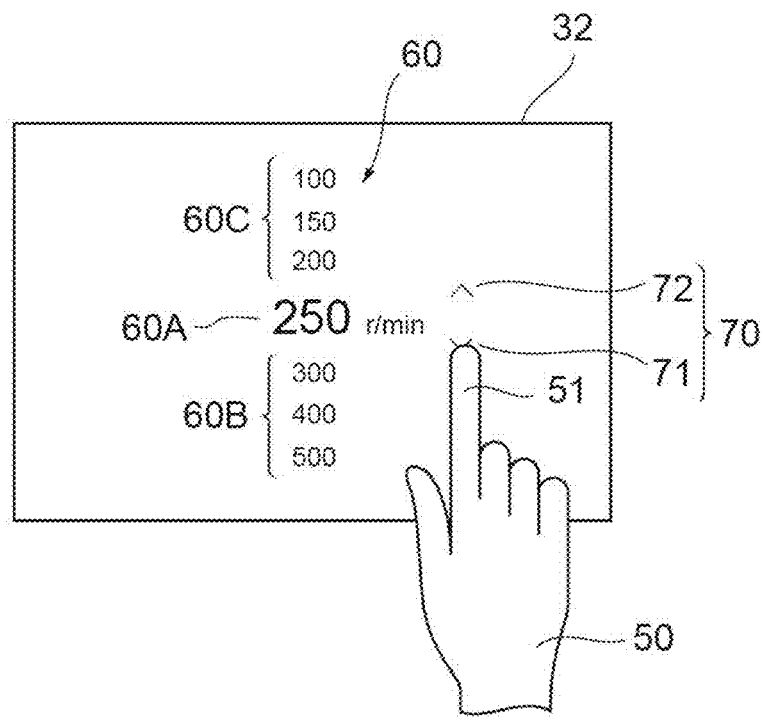
FIG. 11B is a diagram showing another setting example of the first quantitative parameter on the setting screen of FIG. 9B.

In the example, as a quantitative parameter setting operation, there is a choice (alternative operation) other than the swipe operation or the flick operation of the scroll icon 60. Accordingly, as shown in FIG. 11B, the finger 51 of the user 50 touches and taps the increase button 71 or the decrease button 72 of the button icon 70 on the setting screen. In this case, the control unit 31 detects the contact of the finger 51 and the contact time, determines that the button icon 70 has been operated (step S03; YES), and accepts the tap operation (step S04; second accepting step/second accepting process). The control unit 31 changes the quantitative parameter displayed on the scroll icon 60 (step S05). For example, when it is detected that the increase button 71 has been tapped by the finger 51 (refer to FIG. 11B), the control unit 31 performs display control by scrolling the scroll icon 60 so that the larger set value candidates 60B are sequentially displayed at the position of the set value 60A. When it is detected that the decrease button 72 has been tapped by the finger 51, the control unit 31 performs display control by scrolling the scroll icon 60 so that the smaller set value candidates 60C are sequentially displayed at the position of the set value 60A.

In this quantitative parameter change display control, the control unit 31 may perform one (one step) change display each time the increase button 71 or the decrease button 72 is tapped once.

Alternatively, when the finger 51 of the user 50 touches and long-presses the increase button 71 or the decrease button 72 of the button icon 70 on the setting screen for a predetermined period of time or longer, the control unit 31 may detect the contact of the finger 51 and the contact time, determine that the button icon 70 has been operated (step S03; YES), and accept the long press operation (step S04; third accepting step/third accepting process). The control unit 31 changes the quantitative parameter displayed on the scroll icon 60 (step S05). For example, when it is detected that the increase button 71 has been long-pressed by the finger 51, the control unit 31 performs display control by scrolling the scroll icon 60 so that the larger set value candidates 60B are sequentially displayed at the position of the set value 60A. When it is detected that the decrease button 72 has been long-pressed by the finger 51, the control unit 31 performs display control by scrolling the scroll icon 60 so that the smaller set value candidates 60C are sequentially displayed at the position of the set value 60A. For these long press operations, the control unit 31 may perform display control so that the scroll speed increases as the contact time increases.

The control unit 31 may accept a tap operation or a long press operation at an arbitrary position other than the set value 60A of the scroll icon 60. When a tap operation on the position of the larger set value candidate 60B is performed, the control unit 31 may perform display control so that the smaller set value candidate 60C is displayed one by one (one step) at the position of the set value 60A. When a tap operation on the position of the smaller set value candidate 60C is performed, the control unit 31 may perform display control so that the larger set value candidate 60B is displayed one by one (one step) at the position of the set value 60A. When it is detected that the position of the larger set value candidate 60B has been long-pressed by the finger 51, the control unit 31 performs display control by scrolling the scroll icon 60 so that the smaller set value candidates 60C are sequentially displayed at the position of the set value 60A. When it is detected that the position of the smaller set value candidate 60C has been long-pressed by the finger 51, the control unit 31 performs display control by scrolling the scroll icon 60 so that the larger set value candidates 60B are sequentially displayed at the position of the set value 60A. For these long press operations, the control unit 31 may perform display control so that the scroll speed increases as the contact time increases.

When it is determined in step S03 that neither the scroll icon 60 nor the button icon 70 has been operated (step S03; NO), the control unit 31 repeats the determination process of step S03.

Subsequent to step S05, the control unit 31 determines whether or not the OK button 73 or the cancel button 74 has been pressed (step S06). When it is determined that the OK button 73 has been pressed, the control unit 31 stores the set value 60A in the memory 33 as a quantitative parameter (step S07; parameter setting step). Then, the control unit 31 switches the display of the touch panel display 32 to the normal screen (step S08). As a result, the accepting process for a series of operations on the touch panel display 32 ends. When it is determined in step S06 that the cancel button 74 has been pressed, the control unit 31 switches the display of the touch panel display 32 to the normal screen (step S08). When it is determined in step S06 that neither the OK button 73 nor the cancel button 74 has been pressed (step S06; NO), the control unit 31 repeats the determination process of step S03.

Subsequently, other quantitative parameter setting operations and accepting processes for the quantitative parameter setting operations will be described with reference to FIGS. 12 to 15. FIG. 12A is a diagram showing a start-up operation of a setting screen of a second quantitative parameter on the touch panel display 32, and FIG. 12B is a diagram showing the setting screen of the second quantitative parameter. The second quantitative parameter is the torque value of the cutting tool 8. In the following description, the same parts as those described above with reference to FIGS. 9 to 11 will be omitted.

As shown in FIG. 12A, the finger 51 of the user 50 touches and taps the dot display portion 66 indicating the torque value. The screen is switched by the tap operation, and as shown in FIG. 12B, the control unit 31 may cause the touch panel display 32 to simultaneously display the scroll icon 60 and the button icon 70 for the user to set the torque value of the cutting tool 8 in the root canal length measuring device 10 (display step). The value already stored as the torque value is highlighted as the set value 60A. Above the set value 60A, one or more larger set value candidates 60B are displayed. Below the set value 60A, one or more smaller set value candidates 60C are displayed.

The button icon 70 including an increase button 71 and a decrease button 72 is displayed on the side of the scroll icon 60. The scroll direction of the scroll icon 60 is the vertical direction on the screen. The increase button 71 and the decrease button 72 are disposed adjacent to the left side of the figure (in the shown example, a filled bar) indicating the set value 60A included in the scroll icon 60. The increase button 71 and the decrease button 72 are arrayed in the vertical direction of the screen, and the increase button 71 is disposed above the decrease button 72.

Figure 13A:
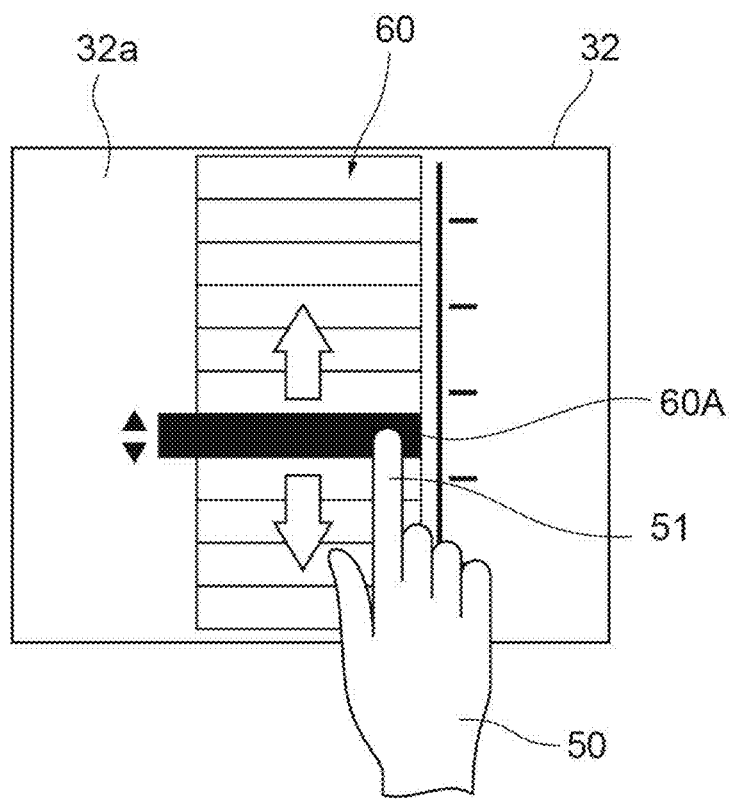
FIG. 13A is a diagram showing a setting example of the second quantitative parameter on the setting screen of FIG. 12B.

As shown in FIG. 13A, the set value 60A moves up and down on the scroll icon 60 by swiping or flicking the scroll icon 60. The swipe operation in this case is a drag-and-drop operation for moving the figure indicating the set value 60A. The figure indicating the set value 60A can be moved to the position to change the set value by tapping an arbitrary position other than the set value 60A on the scroll icon 60.

Figure 13B:
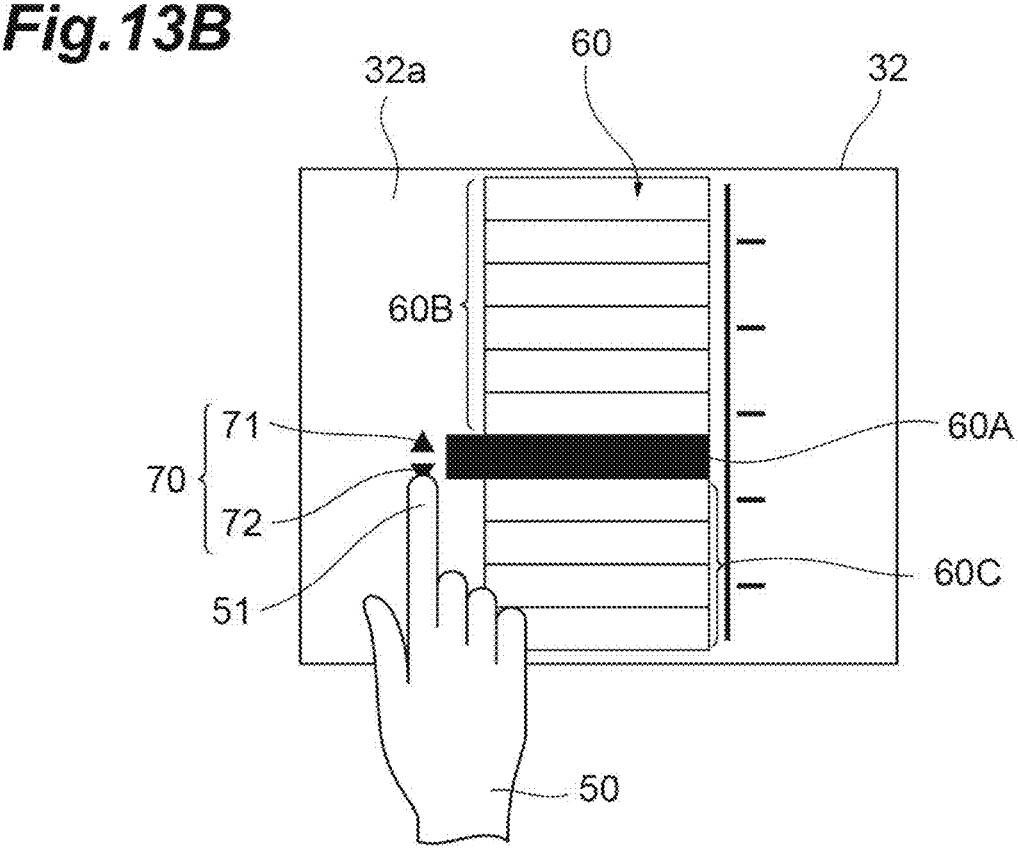
FIG. 13B is a diagram showing another setting example of the second quantitative parameter on the setting screen of FIG. 12B.

As shown in FIG. 13B, a tap operation on the button icon 70 as an alternative operation is possible. By tapping the increase button 71 with the finger 51, the position of the figure indicating the set value 60A moves upward, and the set value of the torque increases. By tapping the decrease button 72 with the finger 51, the position of the figure indicating the set value 60A moves downward, and the set value of the torque decreases. By long-pressing the button icon 70, the movement speed of the position of the figure indicating the set value 60A can be increased.

Figure 14B:
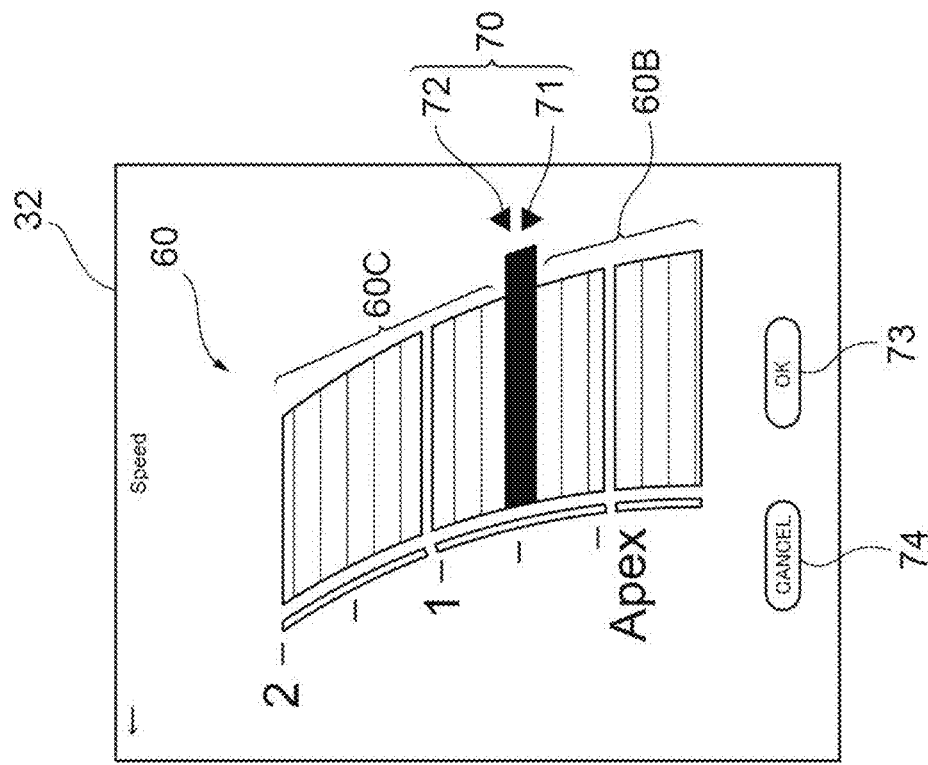
FIG. 14B is a diagram showing the setting screen of the third quantitative parameter.
Figure 14A:
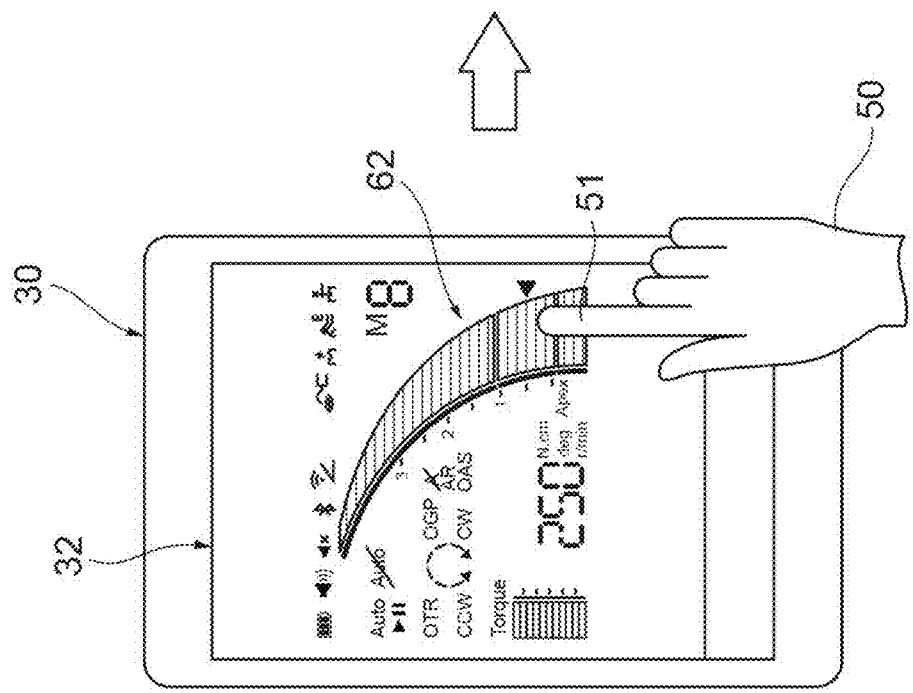
FIG. 14A is a diagram showing a start-up operation of a setting screen of a third quantitative parameter on a touch panel display.

FIG. 14A is a diagram showing a start-up operation of a setting screen of a third quantitative parameter on the touch panel display 32, and FIG. 14B is a diagram showing the setting screen of the third quantitative parameter. The third quantitative parameter is the length (position) of the root canal to automatically stop (auto-stop) the cutting tool 8 or the length (position) of the root canal to automatically reverse (apically reverse) the cutting tool 8.

As shown in FIG. 14A, the finger 51 of the user 50 touches and taps the dot display portion 62 indicating the length (position) of the root canal. The screen is switched by the tap operation, and as shown in FIG. 14B, the control unit 31 may cause the touch panel display 32 to simultaneously display the scroll icon 60 and the button icon 70 for the user to set the length (position) of the root canal in the root canal length measuring device 10 (display step). The value already stored as the length (position) of the root canal is highlighted as the set value 60A. Below the set value 60A, one or more larger set value candidates 60B are displayed. Above the set value 60A, one or more smaller set value candidates 60C are displayed. In addition, in the description of the length of the root canal (root canal length), "large" is synonymous with "deep", and "small" is synonymous with "shallow".

The button icon 70 including an increase button 71 and a decrease button 72 is displayed on the side of the scroll icon 60. The scroll direction of the scroll icon 60 is the vertical direction on the screen. The increase button 71 and the decrease button 72 are disposed adjacent to the right side of the figure (in the shown example, a filled bar) indicating the set value 60A included in the scroll icon 60. The increase button 71 and the decrease button 72 are arrayed in the vertical direction of the screen, and the increase button 71 is disposed below the decrease button 72.

Figure 15A:
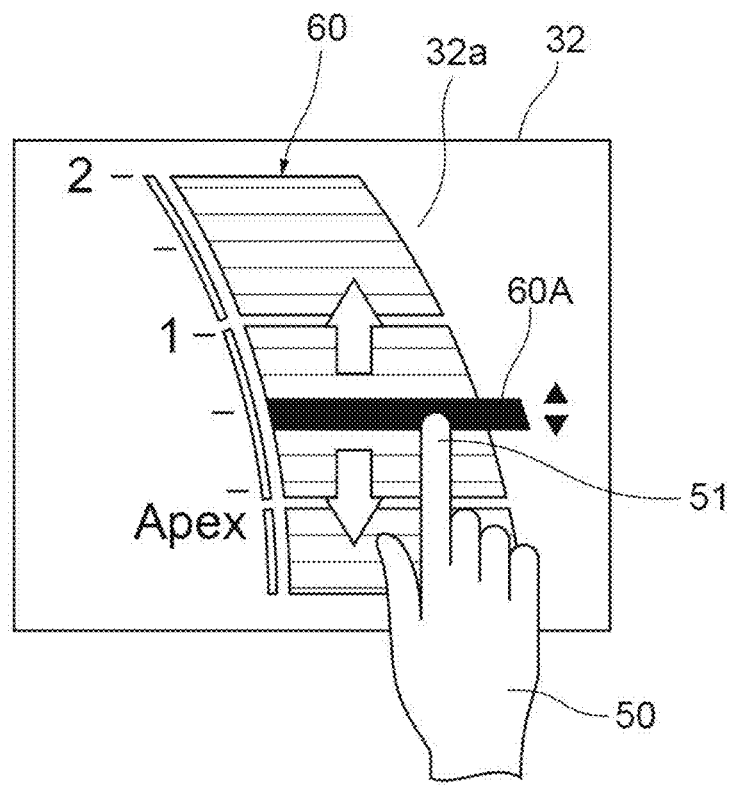
FIG. 15A is a diagram showing a setting example of the third quantitative parameter on the setting screen of FIG. 14B.

As shown in FIG. 15A, the set value 60A moves up and down on the scroll icon 60 by swiping or flicking the scroll icon 60. The swipe operation in this case is a drag-and-drop operation for moving the figure indicating the set value 60A. The figure indicating the set value 60A can be moved to the position to change the set value by tapping an arbitrary position other than the set value 60A on the scroll icon 60.

Figure 15B:
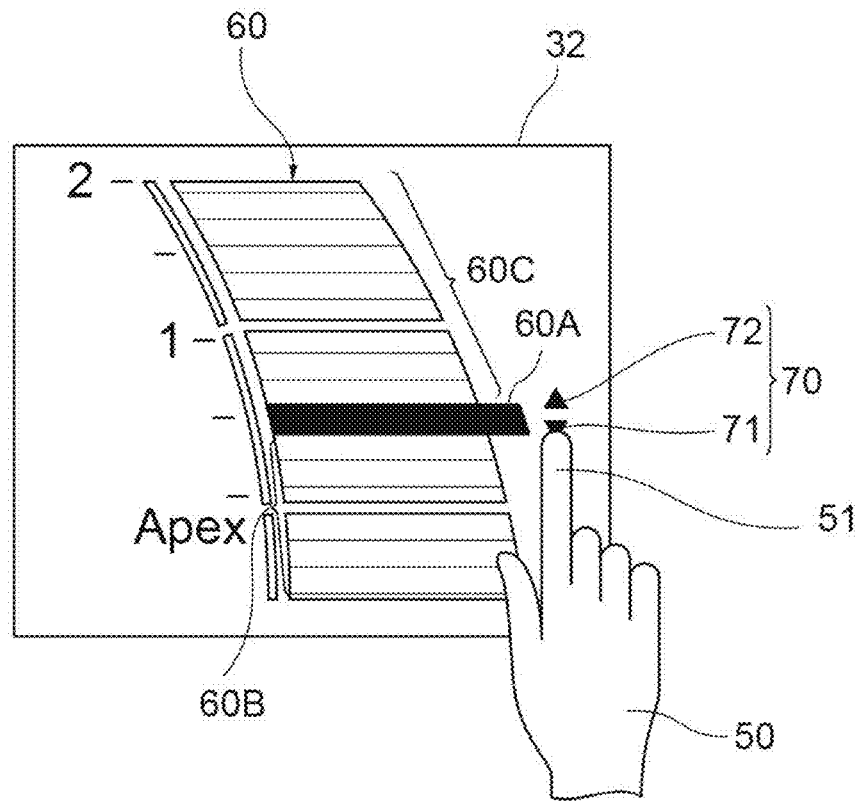
FIG. 15B is a diagram showing another setting example of the third quantitative parameter on the setting screen of FIG. 14B.

As shown in FIG. 15B, a tap operation on the button icon 70 as an alternative operation is possible. By tapping the decrease button 72 with the finger 51, the position of the figure indicating the set value 60A moves upward, and the set value of the length (position) of the root canal is decreased. By tapping the decrease button 72 with the finger 51, the position of the figure indicating the set value 60A moves upward, and the set value of the length (position) of the root canal is decreased. By long-pressing the button icon 70, the movement speed of the position of the figure indicating the set value 60A can be increased.

According to the computer program for the touch panel display 32 and the accepting method of the example described above, the scroll icon 60 and the button icon 70 for the user to set the quantitative parameter are simultaneously displayed on the touch panel display 32. The user can swipe or flick the scroll icon 60 with the finger 51. In the first accepting process, or in the first accepting process, a flick operation is accepted to set the quantitative parameter. Depending on the environment in which the touch panel display 32 is used, it may be difficult to perform such an operation. For example, when the humidity is high or when the user wears a silicone or rubber glove on his or her hand, the fingertip does not slide easily on the screen. Alternatively, the user may not like the operation of scrolling the scroll icon 60. In such a case, in the second accepting process, or in the second accepting process, a tap operation is accepted to set the quantitative parameter. In addition to the operation of sliding the finger 51 on the screen, the quantitative parameter can be set by the operation of pressing the screen with the finger 51. Therefore, the operability of the touch panel display 32 for the user is improved.

When a long press operation on the button icon 70 is detected on the touch panel display 32, the control unit 31 further performs a third accepting process for accepting the long press operation. In the third accepting process, a long press operation is accepted to set the quantitative parameter. As a result, it is possible to display an operation different from the operation based on the tap operation, for example, an operation of scrolling the scroll icon 60 faster. Therefore, the operability of the touch panel display 32 for the user can be further improved.

The button icon 70 includes the increase button 71 and the decrease button 72 that are disposed adjacent to the side of the character indicating the set value 60A included in the scroll icon 60. Since the scroll icon 60 and the increase button 71 and the decrease button 72 of the button icon 70 are disposed at positions close to each other, the operability is excellent even when the operation method is not familiar or the operation method is switched.

According to the tablet 30 including the memory 33 that stores the computer program for the touch panel display 32 of the example, the touch panel display 32, and the control unit 31, it is possible to improve the operability when setting the quantitative parameter.

It is to be understood that not all aspects, advantages and features described herein may necessarily be achieved by, or included in, any one particular example. Indeed, having described and illustrated various examples herein, it should be apparent that other examples may be modified in arrangement and detail. The scroll direction of the scroll icon (movement direction of the set value) may be the left-right direction of the screen. Without being limited to the touch panel display 32 of the tablet 30 as a terminal device, a medical device such as the root canal length measuring device 10 may include a touch panel display, and the computer program or the accepting method of the invention may be applied to the touch panel display.

The invention may be applied to any medical device and any medical system other than dental treatment. The invention can be applied to any device as long as this is a medical device in which quantitative parameters for controlling the medical device can be set using a touch panel display.

What is claimed is:

1. A medical system, comprising:
a medical device; and
a remote control device configured to communicate with the medical device,
wherein the medical device includes:
a first communication interface that transmits data relevant to medical treatment performed in the medical device to the remote control device;
a first display configured to display a figure or a character corresponding to the data, and wherein the medical device is configured to receive a user input designating a volume level of an auditory warning; and
a first controller configured to cause the first display to display the figure or the character corresponding to the data and that, when the data satisfies conditions for notification of a warning, causes the medical device to emit a first warning including at least the auditory warning,
wherein the volume level of the auditory warning emitted from the medical device is prohibited from being set lower than a predetermined, non-zero minimum volume level,
wherein, prior to transmitting the data to the remote control device, the medical system is preset to operate in a plurality of notification modes including a first notification mode and a second notification mode, and
wherein the remote control device includes:
a second communication interface that receives the data from the medical device;
a second display that displays the figure or the character corresponding to the data; and
a second controller configured to:
cause the second display to display the figure or the character corresponding to the data;
determine that the data satisfies the conditions for notification of the warning, by performing a calculation based on one or more values in the data and warning notification conditions stored in the remote control device;
cause the remote control device to emit a second warning including both a visual warning and the auditory warning in response to the determination when the medical system is operating in the first notification mode; and
cause the remote control device to emit the visual warning without emitting the auditory warning in response to the determination when the medical system is operating in the second notification mode, even when the data satisfies the conditions for notification of the warning.

2. The medical system according to claim 1,
wherein the plurality of notification modes additionally includes a third notification mode,
wherein the first controller causes the first display to display the visual warning in the third notification mode when the data satisfies the conditions for notification of the warning, and
wherein the second controller also causes the second display to display the visual warning in the third notification mode when the data satisfies the conditions for notification of the warning.

3. The medical system according to claim 1,
wherein the first controller causes the medical device to emit the first warning including a tactile warning when the data satisfies the conditions for notification of the warning,
wherein the second controller causes the remote control device to emit the second warning including the tactile warning in response to receiving the data when the medical system is operating in the first notification mode, and
wherein the second controller causes the remote control device to emit the visual warning without emitting the tactile warning and without emitting the auditory warning in response to receiving the data when the medical system is operating in the second notification mode, even when the data satisfies the conditions for notification of the warning.

4. The medical system according to claim 1,
wherein the second display of the remote control device includes a touch panel display for operating the medical device, and
wherein the second controller of the remote control device is configured to:
cause the touch panel display to simultaneously display a scroll icon and a button icon for a user to set a quantitative parameter for controlling the medical device;
detect a swipe or flick operation on the scroll icon on the touch panel display;
perform a first accepting process for accepting the swipe or flick operation;
detect a tap operation on the button icon on the touch panel display; and
perform a second accepting process for accepting the tap operation.

5. The medical system according to claim 4, wherein the second controller is further configured to:
detect a long press operation on the button icon on the touch panel display; and
perform a third accepting process for accepting the long press operation.

6. The medical system according to claim 5, wherein the button icon includes an increase function and a decrease function disposed adjacent to the character or the figure indicating a set value included in the scroll icon.

7. The medical system according to claim 1, wherein the first warning emitted from the medical device includes auditory warning and at least one other type of warning selected from the group consisting of the visual warning and a tactile warning.

8. The medical system according to claim 1, wherein the second controller is further configured to display a warning message on the second display indicating that the user input designating the volume level of the auditory warning emitted from the medical device is attempting to be set lower than the predetermined, non-zero minimum volume level.

9. The medical system according to claim 1,
wherein the second controller is further configured to monitor a status of the data relevant to medical treatment in repeatedly determining whether the data satisfies the condition for notification of the first warning, and
wherein the status is overwritten in the second controller in response to receiving new data relevant to medical treatment from the medical device.

10. The medical system according to claim 1,
wherein the medical device comprises a root canal length measuring device, and
wherein the remote control device comprises a tablet.

11. The medical system according to claim 1,
wherein the medical device comprises a cutting tool for performing root canal enlargement, and
wherein the data satisfies the conditions for notification of the warning when a distal end of the cutting tool is located at a predetermined root canal position.

12. A non-transitory memory device of a remote control device having instructions stored thereon that, in response to execution by a controller of the remote control device, cause the controller to perform operations comprising:
processing data received from a medical device communicably coupled to the remote control device;
causing the remote control device to display a figure or a character corresponding to the data received from the medical device while the figure or character is concurrently being displayed on the medical device;
determining that the data satisfies a condition for notification of a first warning emitted from the medical device by performing a calculation based on one or more values in the data and warning notification conditions stored in the remote control device, wherein prior to receiving the data from the medical device, the remote control device is preset to operate in a plurality of notification modes including a first notification mode and a second notification mode when the data satisfies the condition for notification of the first warning emitted from the medical device;
causing the remote control device to emit a second warning including both of a visual warning and an auditory warning, in response to the determination when the remote control device is operating in the first notification mode, wherein the second warning is different than the first warning;
modifying control of the remote control device in order to cause the remote control device to emit the visual warning without emitting the auditory warning in response to the determination when the remote control device is operating in the second notification mode, even when the data satisfies the condition for notification of the first warning; and
displaying a warning message on the remote control device indicating that a user input designating a volume level of the auditory warning included in the first warning emitted from the medical device is attempting to be set lower than a predetermined, non-zero minimum volume level.

13. The non-transitory memory device according to claim 12, wherein the first warning emitted from the medical device includes the auditory warning and at least one other type of warning selected from the group consisting of the visual warning and a tactile warning.

14. The non-transitory memory device according to claim 13,
wherein the second warning emitted from the remote control device consists of three types of warnings including the visual warning, the auditory warning, and the tactile warning when the medical system is operating in the first notification mode,
wherein the remote control device emits the visual warning without emitting the auditory warning and without emitting the tactile warning, when the medical device is operating in the second notification mode, even when the data satisfies the condition for notification of the first warning, and
wherein the remote control device emits the visual warning while the medical device emits the first warning, in both the first notification mode and the second notification mode.

15. The non-transitory memory device according to claim 12,
wherein the controller is further configured to monitor a status of the data relevant to medical treatment in repeatedly determining whether the data satisfies the condition for notification of the first warning, and
wherein the status is overwritten in the controller in response to receiving new data relevant to medical treatment from the medical device.

16. The non-transitory memory device according to claim 12,
wherein the medical device comprises a root canal length measuring device, and
wherein the remote control device comprises a tablet.

17. The non-transitory memory device according to claim 12,
wherein the medical device comprises a cutting tool for performing root canal enlargement, and
wherein the data satisfies the condition for notification of the first warning when a distal end of the cutting tool is located at a predetermined root canal position.

18. A medical system, comprising:
a root canal length measuring device; and
a remote control device configured to communicate with the root canal length measuring device,
wherein the root canal length measuring device includes:
a cutting tool for performing a root canal enlargement;
a first communication interface that transmits data relevant to the root canal enlargement to the remote control device;
a first display configured to display a figure or a character corresponding to the data, and wherein the root canal length measuring device is configured to receive a user input designating a volume level of an auditory warning; and
a first controller configured to cause the first display to display the figure or the character corresponding to the data and that, when the data satisfies conditions for notification of a warning, causes the root canal length measuring device to emit a first warning including at least the auditory warning,
wherein the volume level of the auditory warning emitted from the root canal length measuring device is prohibited from being set lower than a predetermined, non-zero minimum volume level,
wherein, prior to transmitting the data to the remote control device, the root canal length measuring device is preset to operate in a plurality of notification modes including a first notification mode and a second notification mode, and wherein the remote control device includes:
- a second communication interface that receives the data from the root canal length measuring device;
- a second display that displays the figure or the character corresponding to the data; and
- a second controller configured to:
  - cause the second display to display the figure or the character corresponding to the data;
  - determine that the data satisfies the conditions for notification of the warning when a distal end of the cutting tool is located at a predetermined root canal position;
  - cause the remote control device to emit a second warning including both a visual warning and the auditory warning in response to the determination when the root canal length measuring device is operating in the first notification mode; and
  - cause the remote control device to emit the visual warning without emitting the auditory warning in response to the determination when the root canal length measuring device is operating in the second notification mode, even when the data satisfies the conditions for notification of the warning.

19. The medical system according to claim 18, wherein the remote control device comprises a tablet.

20. The medical system according to claim 18, wherein the second controller is further configured to display a warning message on the second display indicating that the user input designating the volume level of the auditory warning emitted from the root canal length measuring device is attempting to be set lower than the predetermined, non-zero minimum volume level.

* * * * *